(12) United States Patent
Kurogama et al.

(10) Patent No.: US 6,414,751 B1
(45) Date of Patent: Jul. 2, 2002

(54) DISPLACEMENT MEASUREMENT APPARATUS

(75) Inventors: Tatsuji Kurogama; Norikazu Arai; Makoto Banno, all of Hachioji (JP)

(73) Assignee: Konica Corporation, Tokyo (JP)

( * ) Notice: Subject to any disclaimer, the term of this patent is extended or adjusted under 35 U.S.C. 154(b) by 0 days.

(21) Appl. No.: 09/643,252

(22) Filed: Aug. 22, 2000

(30) Foreign Application Priority Data

Aug. 24, 1999 (JP) .......................................... 11-236600

(51) Int. Cl.⁷ .............................................. G01N 21/00
(52) U.S. Cl. ................................ 356/237.1; 356/237.6; 356/614
(58) Field of Search ................................ 356/600, 614, 356/622, 623, 624, 237.1, 237.2, 237.3, 237.4, 237.5, 237.6, 429–431; 250/559.29, 559.34, 559.42, 559.45

(56) References Cited

U.S. PATENT DOCUMENTS

| 4,377,340 A | * | 3/1983 | Green et al. ................ 356/237 |
| 4,560,273 A | * | 12/1985 | Ando et al. .................. 356/237 |
| 5,469,294 A | * | 11/1995 | Wilt et al. ................... 359/436 |
| 5,963,316 A | * | 10/1999 | Miura et al. ............. 356/237.3 |
| 6,097,482 A | * | 8/2000 | Smith et al. ............. 356/237.1 |
| 6,122,042 A | * | 9/2000 | Wunderman et al. ......... 356/73 |
| 6,198,533 B1 | * | 3/2001 | Meeks et al. ................ 356/381 |

FOREIGN PATENT DOCUMENTS

WO  WO 99/44039  * 9/1999

* cited by examiner

Primary Examiner—Hoa Q. Pham
(74) Attorney, Agent, or Firm—Finnegan, Henderson, Farabow, Garrett & Dunner, L.L.P.

(57) ABSTRACT

A surface displacement detecting apparatus for detecting a concave, a hole on a surface of a detection object, comprises a light shielding device provided in a direction crossing the surface of the detection object, a light irradiating device provided at one side of the light shielding device and to irradiate the detection object with light; a light receiving device provided at the other side of the light shielding device and to receive at least one of regular reflection light and diffuse reflection light from the surface of the detection object; and a conveyor to convey at least one of the detection object and the light irradiating device.

21 Claims, 18 Drawing Sheets

FIG. 5
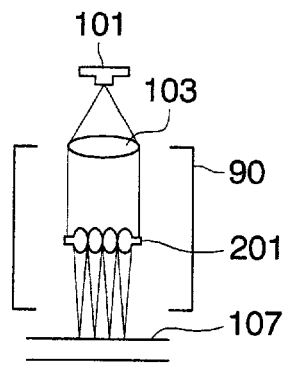
FIG. 6(a)   FIG. 6(b)
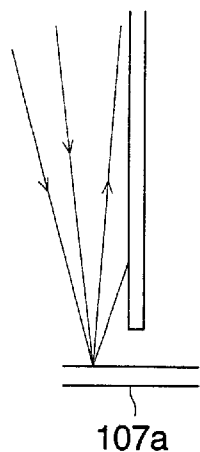 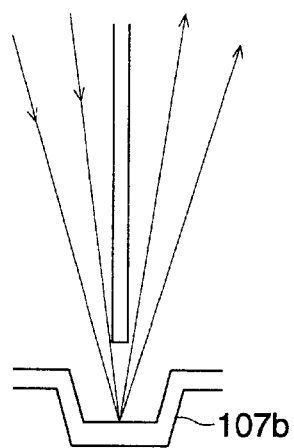
FIG. 7
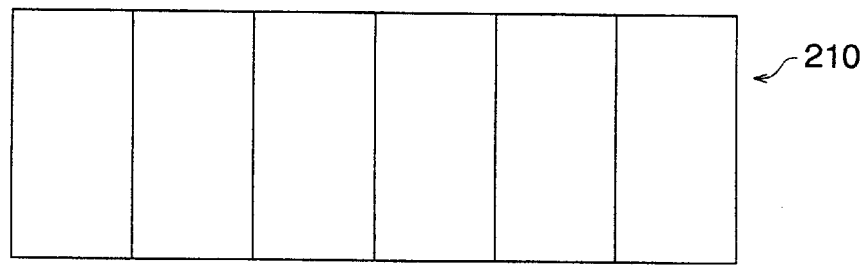

| | EXAMPLE OF 7TH EMBODIMENT | EXAMPLE OF 8TH EMBODIMENT |
|---|---|---|
| FLAT PORTION | A B C | A B C |
| IRREGULAR PORTION | | |
| $\dfrac{(A+C)-B}{A+B+C}$ | SENSITIVITY, MEDIUM | SENSITIVITY, HIGH |

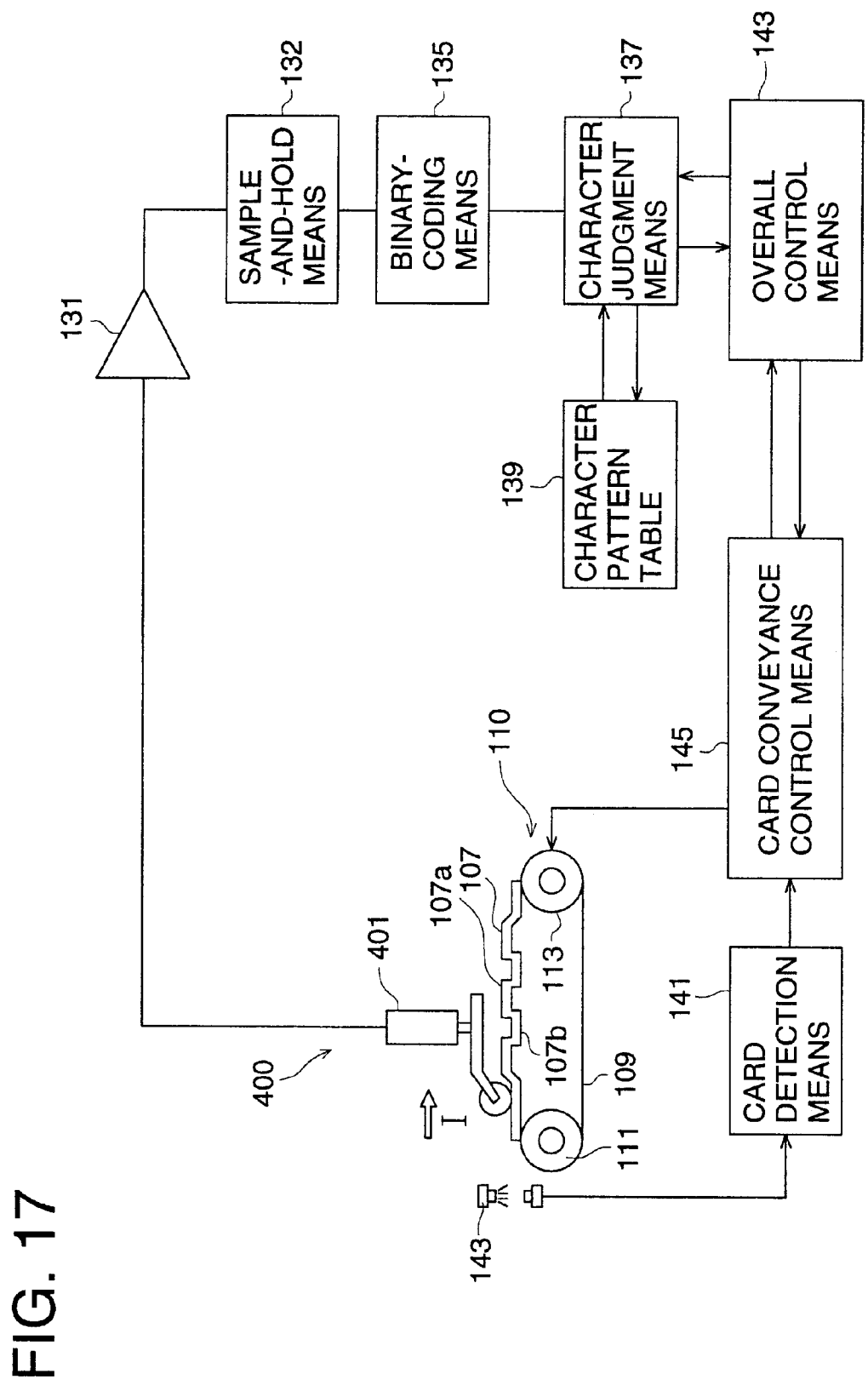

DISPLACEMENT MEASUREMENT APPARATUS

BACKGROUND OF THE INVENTION

The present invention relates to a displacement measurement apparatus which detects displacement distribution in the direction of a height of a convex portion or a concave portion formed on the surface of a card.

There is available a detection apparatus of an optical system for displacement on the surface having the structure shown in FIG. 23, as an apparatus for detecting displacement distribution in the direction of a height formed on the surface of an object to be inspected.

In the drawing, the numeral 1 represents a linear light source which emits linear light.

As shown in FIG. 24, the linear light source 1 is composed of light source 3 and cylindrical cover 7 which contains the light source 3 and has on its end surface slit 5 representing a linear light generating means.

In FIG. 23 again, a linear light emitted from the linear light source 1 is projected on object to be inspected 11 through rotary mirror 9 serving as a scanning means.

Reflected light from the object to be inspected 11 enters PSD (semiconductor position detection element) array 13 divided into plural pieces in the linear direction of the linear light, and thereby, displacement distribution on the surface of the object to be inspected 11 is detected.

In recent years, there has spread a card 21 having an arrangement shown in FIG. 25.

The numeral 23 represents a magnetic stripe on which magnetic information is recorded, and 25 represents a character row formed by a convex portion or a concave portion (12345678910, Konica Tarou, in FIG. 25).

When reading a convex portion or a concave portion (displacement in the direction of a height on the surface) on card 21 by the use of the detection apparatus of an optical system for displacement on the surface, if the card 21 has been subjected to printing and reflectance for light on the surface of the card 21 has been lowered accordingly, the convex portion or the concave portion can not be read accurately, which is a problem.

SUMMARY OF THE INVENTION

The invention has been achieved in view of the problem mentioned above, and its object is to provide a displacement measurement apparatus wherein a convex portion or a concave portion on a card can be read accurately even in the case of a card having poor reflectance.

The above object can be attained by the following structures.

Structure (1-1) A surface displacement detecting apparatus for detecting a concave, a convex or a hole on a surface of a detection object, comprises:

a light shielding device provided in a direction crossing the surface of the detection object, a light irradiating device provided at one side of the light shielding device and to irradiate the detection object with light;

a light receiving device provided at the other side of the light shielding device and to receive at least one of regular reflection light and diffuse reflection light from the surface of the detection object; and a conveyor to convey at least one of the detection object and the light irradiating device.

Structure (1-2) In the surface displacement detecting apparatus of (1-1), the light irradiating device comprises a light source and an optical element to irradiate the detection object with the light emitted from the light source and the light receiving device comprises a condenser lens to condense at least one of the regular reflection light and the diffuse reflection light from the surface of the detection object and a light receiving element to receive the condensed light.

Structure (1-3) In the surface displacement detecting apparatus of (1-2), the light irradiating device shapes the light in a line and irradiates the detection object with the line-shaped light.

Structure (1-4) In the surface displacement detecting apparatus of (1-2), the optical element is a cylindrical lens.

Structure (1-5) In the surface displacement detecting apparatus of (1-2), the light irradiating device forms a plurality of spot light aligned in a straight line as the light and irradiates the detection object with the plurality of spot light.

Structure (1-6) In the surface displacement detecting apparatus of (1-5), wherein the optical element is a micro lens array.

Structure (1-7) In the surface displacement detecting apparatus of (1-1), wherein the detection object comprises a flat surface and a concave and the light irradiating device, the light shielding device and the light receiving device are arranged such that light reflected from the flat surface is shielded by the light shielding device and light reflected from the concave proceeds to the light receiving element.

Structure (1-8) In the surface displacement detecting apparatus of (1-1), the detection object comprises a flat surface and a concave and the light irradiating device, the light shielding device and the light receiving device are arranged such that light diffused from the flat surface is shielded by the light shielding device and light diffused from the concave proceeds to the light receiving element.

Structure (1-9) In the surface displacement detecting apparatus of (1-1), the width of the light on the detection object is smaller than the width of the concave, the convex or the hole.

Structure (1-10) In the surface displacement detecting apparatus of (1-2), the surface displacement detecting apparatus detects the concave, the convex or the hole from a light receiving position on the light receiving element.

Structure (1-11) In the surface displacement detecting apparatus of (1-2), the light receiving device comprises a plurality of light receiving elements aligned in a straight line as the light receiving element or the light receiving element is split into a plurality of light receiving elements aligned in a straight line.

Structure (1-12) In the surface displacement detecting apparatus of (1-2), the light receiving elements are a PSD array in which n pieces of PSD are arranged in a predetermined direction or PD which is split into n pieces in a predetermined direction and into m pieces in a direction perpendicular to the predetermined direction, where n is an integer not less than 2 and m is an integer not less than 1.

Structure (1-13) In the surface displacement detecting apparatus of (1-3), the light receiving elements are a PSD array in which n pieces of PSD are arranged in a direction along the line-shaped light or PD which is split into n pieces in a direction along the line-shaped light and m pieces in a direction perpendicular to along the line-shaped light, where n is an integer not less than 2 and into m is an integer not less than 1.

Structure (1-14) In the surface displacement detecting apparatus of (1-5), the light receiving elements are a PSD array in which n pieces of PSD are arranged in a direction along the plurality of aligned spot light or PD which is split into n pieces in a direction along the plurality of aligned spot light and into m pieces in a direction perpendicular to along the plurality of aligned spot light, where n is an integer not less than 2 and m is an integer not less than 1.

Structure (1-15) In the surface displacement detecting apparatus of (1-1), the light shielding device is shiftable in a direction crossing the surface of the detection object and the light shielding device is brought in contact with the detection object.

Structure (1-16) In the surface displacement detecting apparatus of (1-1), the light shielding device has an edge surface facing the detection object and is arranged to form a space between the edge surface and the detection object.

Structure (1-17) In the surface displacement detecting apparatus of (1-10), the light receiving position on the light receiving element displaces in a direction parallel to the light receiving element.

Structure (1-18) In the surface displacement detecting apparatus of (1-1), the detection object is a card having the concave, the convex or the hole.

Structure (1-19) In the surface displacement detecting apparatus of (1-1), a range of the displacement of the concave, the convex or the hole on the detection object is not larger than 1.0 mm.

Structure (1-20) In the surface displacement detecting apparatus of claim 1, the surface displacement detecting apparatus detects an amount of the displacement of the concave, the convex or the hole.

Structure (1-21) An optical pickup apparatus for use in a surface displacement detecting apparatus for detecting a concave, a convex or a hole on a surface of a detection object, comprises:

a light shielding device provided in a direction crossing the surface of the detection object, a light irradiating device provided at one side of the light shielding device and to irradiate the detection object with light; and a light receiving device provided at the other side of the light shielding device and to receive at least one of regular reflection light and diffuse reflection light from the surface of the detection object.

There will be explained another embodiment wherein discrimination between a flat portion and a concave portion, or a convex portion, or a hole portion is easy even in the case of a card having poor reflectance for light. Incidentally, it is possible to combine the following structures with the invention at any time, or to combine the following embodiments themselves.

Structure (2-1)

A surface displacement detection apparatus comprising plural contact type displacement detection sensors, wherein aforesaid plural contact type displacement detection sensors are arranged to be in a two-dimensional form, and the plural contact type displacement detection sensors are in contact with an object to be inspected so that a concave portion, a convex portion or a hole portion of the object to be inspected is detected.

Structure (2-2)

The surface displacement detection apparatus according to Structure (2-1), wherein the object to be inspected stated above is a card having a concave portion, a convex portion or a hole portion.

Structure (2-3)

The surface displacement detection apparatus according to Structure (2-1), wherein a range of displacement of a concave portion, a convex portion or a hole portion of the object to be inspected stated above is not more than 1.0 mm.

Structure (2-4)

The surface displacement detection apparatus according to Structure (2-1), wherein an amount of displacement of a concave portion, a convex portion or a hole portion of the object to be inspected is detected by the aforesaid surface displacement detection apparatus.

Structure (2-5)

The surface displacement detection apparatus according to Structure (2-1), wherein a width of one of the aforesaid contact type displacement detection sensors is smaller than that of a concave portion, a convex portion or a hole portion of the object to be inspected.

Structure (2-6)

The surface displacement detection apparatus according to Structure (2-1) having therein a pattern recognition section which recognizes patterns on the surface of the object to be inspected from information of a concave portion, a convex portion or a hole portion of the object to be inspected.

Structure (2-7)

The surface displacement detection apparatus according to Structure (2-1), wherein the contact type displacement detection sensor recognizes a concave portion, a convex portion or a hole portion of the object to be inspected by the fluctuation of a value of resistance.

Structure (2-8)

The surface displacement detection apparatus according to Structure (2-1), wherein the contact type displacement detection sensor recognizes a concave portion, a convex portion or a hole portion of the object to be inspected by the fluctuation of a value of electrostatic capacity.

Structure (2-9)

The surface displacement detection apparatus according to Structure (2-1), wherein the contact type displacement detection sensor is a linear encoder.

Structure (2-10)

A method of detecting a concave portion, a convex portion or a hole portion of the object to be inspected comprising a step to bring an object to be inspected into contact with the surface displacement detection apparatus and a step to detect a concave portion, a convex portion or a hole portion of the object to be inspected, wherein a surface displacement detection apparatus has plural contact type displacement detection sensors which are arranged to be in the two-dimensional form, and the plural contact type displacement detection sensors come in contact with an object to be inspected to detect a concave portion, a convex portion or a hole portion of the object to be inspected.

The invention described in Structure (3-1) to solve the problems stated above is represented by a displacement measurement apparatus composed of a light-shielding means which is provided in the direction to cross the surface of the card above that card on which the characters are formed by convex portions or concave portions, a light irradiating means which is provided on one side of the light-shielding means and projects linear light on the card, a light-receiving means which is provided on the other side of the light-shielding means and receives at least one of a regular reflected light on the surface of the card and a diffused light, and of a conveyance means which conveys at least one of the card and the light irradiating means in the direction to cross the direction of a line of the linear light.

When a leading edge portion of the light-shielding means is provided to be located in the vicinity of the surface (flat portion) of the card under the condition that a character is formed by a concave portion, regular reflected light and diffused light on the flat section are cut by the light-shielding means more, compared with regular reflected light and diffused light on the concave portion, thus, a central position and an angle of an effective incident light are changed when the incident light enter the light-receiving means.

Accordingly, discrimination between the flat portion and the concave portion is easy even in the case of a card having poor reflectance for light.

Further, when a leading edge portion of the light-shielding means is provided to be located in the vicinity of the convex portion of the card under the condition that a character is formed by a convex portion, regular reflected light and diffused light on the convex portion are cut by the light-shielding means more, compared with regular reflected light and diffused light on the flat portion, thus, a central position and an angle of an effective incident light are changed when the incident light enter the light-receiving means.

Accordingly, discrimination between the flat portion and the concave portion is easy even in the case of a card having poor reflectance for light.

The invention described in Structure (3-2) is a displacement measurement apparatus wherein the light irradiating means described in Structure (3-1) has a cylindrical lens and irradiates a linear light on the card mentioned above.

By using a cylindrical lens, it is possible to achieve cost reduction.

The invention described in Structure (3-3) is a displacement measurement apparatus wherein the light irradiating means of the invention described in Structure (3-1) has a micro-lens array, and plural spotlight beams arranged mostly on a straight line are irradiated on the aforesaid card.

When intensity of a light source is distributed sharply, intensity of an individual spotlight can be adjusted individually by a lens area, so that uniform spotlight can be irradiated.

Further, by using a micro-lens array, it is also possible to employ a beam size method wherein judgment is made by a diameter of a beam arriving at a light-receiving means, when discriminating a flat portion, a convex portion or a convex portion of a card.

The invention described in Structure (3-4) is a displacement measurement apparatus wherein a card of the invention described in either one of Structure (3-1)–Structure (3-3) is composed of a flat portion and a concave portion, and the light irradiating means and the light-shielding means are arranged so that a reflected light from the flat portion is interrupted by the light-shielding means and a reflected light from the concave portion advances to the light-receiving means.

By arranging the light irradiating means and the light-shielding means so that the regular reflected light reflected on the flat portion is interrupted by the light-shielding means and a regular reflected light reflected on the concave portion advances to the light-receiving means, discrimination between the flat portion and the concave portion is easy because it is possible to select a concave portion if a regular reflected light comes, and to select a flat portion if a regular reflected light does not come.

The invention described in Structure (3-5) is a displacement measurement apparatus wherein the card of the invention described in either one of Structure (3-1)–Structure (3-3) is composed of a flat portion and a concave portion, and the light irradiating means and the light-shielding means are arranged so that a diffused light from the flat portion is interrupted by the light-shielding means and only a diffused light from the concave portion advances to the light-receiving means.

By arranging the light irradiating means and the light-shielding means so that a diffused light from the flat portion is interrupted by the light-shielding means and only a diffused-light from the concave portion advances to the light-receiving means, discrimination between the flat portion and the concave portion is easy because it is possible to select a concave portion if a diffused light comes, and to select a flat portion if a diffused light does not come.

Unlike the regular reflected light, the diffused light is uniformly diverged at a certain solid angle.

Therefore, a degree of freedom of a position of the light-receiving means is enhanced, which makes it possible to discriminate between a flat portion and a concave portion or between a flat portion and a convex portion.

The invention described in Structure (3-6) is a displacement measurement apparatus wherein a width of a linear light from the light irradiating means described in either one of Structure (3-1)–Structure (3-3) is smaller than a width of the convex portion or of the concave portion.

By making a width of a linear light from the light irradiating means to be smaller than a width (preferably, the smallest width) of the convex portion or of the concave portion, it is possible to generate the condition wherein the linear light is projected on the convex portion or the concave portion, and is not projected on the flat portion.

It is therefore easy to detect a convex portion, a concave portion or a flat portion, reading accuracy for a concave portion or a convex portion is improved.

The invention described in Structure (3-7) is a displacement measurement apparatus wherein the light-receiving means of the invention described in either one of Structure (3-1)–structure (3-6) is either one of PD divided into the number n (n represents integers of 2 or more) in the linear direction of the linear light and divided into the number m (m represents integers of 1 or more) in the direction crossing the linear direction and PSD array arranged in quantity of n (n represents integers of 2 or more) in the linear direction of the linear light.

By using either one of PD divided into the number n (n represents integers of 2 or more) in the linear direction of the linear light and divided into the number m (m represents integers of 1 or more) in the direction crossing the linear direction and PSD array arranged in quantity of n in the linear direction of the linear light, it is possible to obtain information not only of intensity of light to be received but also of the central position of brightness of light to be received, and thereby, reading accuracy for a flat portion, a concave portion or a convex portion is improved.

The invention described in Structure (3-8) is a displacement measurement apparatus wherein the light-shielding means of the invention described in either one of Structure (3-1)–Structure (3-7) is provided to be movable in the direction almost crossing the surface of the card and is brought into contact with the surface of the card.

Since the light-shielding means is provided to be movable in the direction almost crossing the surface of the card and is brought into contact with the surface of the card, the light-shielding means can move while tracing the surface of the card to conduct light-shielding even when the card is bent or even when a thin IC chip is provided on the surface of the card. Thus, reading accuracy for a flat portion and a concave portion or a flat portion and a convex portion is improved.

The invention described. in Structure (3-9) is a displacement measurement apparatus wherein the light-shielding means of the invention described in either one of Structure (3-1)–Structure (3-7) has a contact portion which is brought into contact with a portion other than the aforesaid card so that a clearance may be formed between an end surface facing the card and the surface of the card.

Since there is provided a contact portion which is brought into contact with a portion other than the aforesaid card so that a clearance may be formed between an end surface facing the card and the surface of the card, even when the card is bent or a thin IC chip is provided on the surface of the card, the light-shielding means does not interfere with the card, and reading of a flat portion and a concave portion or a flat portion and a convex portion can be conducted.

The invention described in Structure (3-10) is a displacement measurement apparatus having therein a light irradiating means which irradiates a linear light on a card having on its surface a character formed by a convex portion or a concave portion, a light-receiving means which receives at least one of a regular reflected light and a diffused light on the surface of the card, and a conveyance means which conveys at least one of the card and the light irradiating means in the direction crossing the linear direction of the linear light, wherein, the light-receiving means has PD array whose light-receiving surface is divided into two, and is provided so that light from a flat portion of the card may irradiate a light-receiving surface on one side of the two divided light-receiving surfaces and light from the convex portion of the concave portion may irradiate both of the two divided light-receiving surfaces.

If an arrangement is made so that light from a flat portion of the card may irradiate both light-receiving surfaces of the two divided light-receiving surfaces and light from a convex portion or a concave portion may irradiate a light-receiving surface on one side of the two divided light-receiving surfaces, in opposition to the case where light from a flat portion of the card may irradiate a light-receiving surface on one side of the two divided light-receiving surfaces and light from the convex portion of the concave portion may irradiate both of the two divided light-receiving surfaces, it is possible to obtain signals having no connection with light intensity by taking a value of $(A-B)/(A+B)$ when two divided light-receiving surfaces are represented respectively by A and B, and it is possible to read a convex portion or a concave portion accurately even when the reflectance of light on the surface of the card is lowered.

When a circuit to operate division of $(A-B)/(A+B)$ complicated and expensive, APC (automatic power control) is applied on a light source so that output of A or B may always be constant, and a value of $(A-B)$ only is outputted. Due to this, it is possible to obtain the same results as in division on a pseudo basis.

Further, when division of the light-receiving surface is made to be asymmetric, higher sensitivity is obtained.

The invention described in Structure (3-11) is a displacement measurement apparatus having therein a light irradiating means which irradiates a linear light on a card having on its surface a character formed by a convex portion or a concave portion, a light-receiving means which receives at least one of a regular reflected light and a diffused light on the surface of the card, and a conveyance means which conveys at least one of the card and the light irradiating means in the direction crossing the linear direction of the linear light, wherein, the light-receiving means has PD array whose light-receiving surface is divided into three.

When there are formed two portions (for example, a black portion and a white portion) each having different reflectance on the card through printing, there is a fear that even a flat portion is misjudged to be a convex portion or a concave portion. However, when a value of $((A+C)-B)/(A+B+C)$ is taken under the assumption that output of three divided light-receiving surfaces are represented respectively by A, B and C, even when reflectance in the vicinity of a convex portion or a concave portion is fluctuated sharply, misjudgment is lessened because output corresponding to unevenness is performed without being influenced by sharp fluctuation of reflectance.

In place of operating division of $((A+C)-B)/(A+B+C)$, APC (automatic power control) is applied on a light source so that output of $(A+C)$ or of B may always be constant. Then, a value of $(A+C)-B$ only is outputted. Due to this, it is possible to obtain the same output results as in division on a pseudo basis. In particular, when $(A+C)$ is made to be constant, fluctuation of reflectance caused by various patterns on the card tends not to be caused. On this point, an effect of the invention described in Structure 11 is much higher than that of the invention described in Structure 10.

Though a value of $((A+C)-B)$ only is outputted for sharp fluctuation of unevenness, only this makes output to be changed sharply by the change of unevenness, which makes it easy to compare a flat surface with unevenness.

The invention described in Structure (3-12) is a displacement measurement apparatus wherein the light irradiating means of the invention described in Structure (3-10) or in Structure (3-11) has therein a light source, a light-shielding plate which is provided in a parallel light flux emitted from the light source and made to be a parallel light flux, and splits the parallel light flux into two light fluxes, and a lens which condenses the aforesaid two light fluxes on the card.

If two light fluxes are made to coincide with each other on either a flat portion of the card or a concave portion or a convex portion on one side, two light fluxes exist on the remote portion on the other side.

Therefore, by using a light-receiving element whose light-receiving surface is split into two or three, it is possible to detect a convex portion or a concave portion.

When light is condensed on a flat portion, if PD whose light-receiving surface is split into three is used, light is condensed on the central light-receiving surface among three split light-receiving surfaces and misjudgment to cause no misjudgment, even when two portions (for example, a black portion and a white portion) each having different reflectance are formed on the card through printing.

Incidentally, as an optical system of this kind, a telecentric optical system wherein a distance of a reading optical system is proportional to a distance between two beams is more preferable.

The invention described in Structure (3-13) is a displacement measurement apparatus wherein the light irradiating means of the invention described in Structure (3-11) has therein two light sources each emitting a parallel light flux and two lenses each converging each of two light fluxes on the card.

If light converging is conducted on either a flat portion of the card or a concave portion or a convex portion on one side, two light fluxes exist on the portion on the other side.

Therefore, by using a light-receiving element whose light-receiving surface is split into two or three, it is possible to detect a convex portion or a concave portion.

When light is condensed on a flat portion, if PD whose light-receiving surface is split into three is used, light is condensed on the central light-receiving surface among three split light-receiving surfaces and misjudgment to cause no misjudgment, even when two portions (for example, a black portion and a white portion) each having different reflectance are formed on the card through printing.

When realizing a telecentric optical system by using one light source, its design is somewhat difficult. However, by providing each light source, it is possible to realize an inexpensive and accurate optical system which conducts telecentric behaviors.

The invention described in Structure (3-14) is a displacement measurement apparatus having therein a light irradiating means which irradiates linear light on a card having on its surface a character formed by a convex portion or a concave portion, a light-receiving means which receives at least one of regular reflected light and diffused light on the surface of the card and a conveyance means which conveys at least one of the card and the light irradiating means in the direction crossing the linear direction of the linear light, wherein the light irradiating means has a micro-lens array and irradiates, on the card, spotlight beams arranged almost in a straight line, and the light-receiving means has a micro-lens array corresponding to the spotlight beams and PD whose light-receiving surface is split into multiple concentric circles so that each of the concentric circles may correspond to each micro-lens array.

When a light flux coming out of each lens of the micro-lens array is detected through a beam size method by using PD whose light-receiving surface is split into two or more concentric circles, discrimination between a flat portion and a concave portion is easy even when a change in light to be received is great and reflectance of light on the card is poor.

The invention described in Structure (3-15) is a displacement measurement apparatus having therein a contact means having a contact type displacement detection sensor which is brought into contact with a card having on its surface a character formed by a convex portion or a concave portion, and a conveyance means which conveys at least one of the card and the contact means.

By detecting directly a flat portion and a convex portion or a concave portion of the card, discrimination between a flat portion and a concave portion is easy even in the case of a card having poor reflectance of light.

A contact type displacement detection sensor includes one wherein a resistance value is changed depending on the position of a contact like in the invention described in Structure (3-16), and one wherein an electrostatic capacity is changed depending on the position of a contact like in the invention described in Structure (3-17).

The invention described in Structure (3-18) is a displacement measurement apparatus having therein a contact means which is provided to be in contact with a card having on its surface a character formed by a convex portion or a concave portion, and in which plural contact type displacement detection sensors are arranged on a two-dimensional basis on at least a portion where the character is formed.

By detecting directly a flat portion and a convex portion or a concave portion of the card, discrimination between a flat portion and a concave portion or a convex portion is easy despite the card having poor reflectance of light.

Due to the contact means which is provided to be in contact with a card having on its surface a character formed by a convex portion or a concave portion, and in which plural contact type displacement detection sensors are arranged on a two-dimensional basis on at least a portion where the character is formed, detection can be conducted at a time, and a conveyance means which conveys at least one of the card and the contact means is made to be unnecessary.

The invention described in Structure (3-19) is a displacement measurement apparatus having therein a light irradiating means which irradiates light having directivity on a card having on its surface a character formed by a convex portion of a concave portion, a converging lens which condenses regular reflected light on a flat portion other than a convex portion and a concave portion on the card, and a light-receiving means which is provided at the position which is conjugate for the surface of the card through the converging lens, and at which the regular reflected light condensed by the converging lens enters.

Among light irradiated on the card, light reflected on the flat portion other than a convex portion or a concave portion is condensed by the converging lens and advances to the light-receiving means, while, light reflected on a convex portion or a concave portion advances to a destination other than the light-receiving means, especially in the case of a curved surface which is different from a flat surface of a flat portion, such as the case where the sectional form on the surface is almost a circular arc like a convex portion or a concave portion formed through embossing.

Accordingly, the portion where the light-receiving means does not receive light, or the portion where the light-receiving signals are small can be judged in terms of existence as a convex portion or a concave portion on the card.

The invention described in Structure (3-20) is a displacement measurement apparatus according to Structure (3-19) wherein the light-irradiating means described in Structure (3-19) irradiates linear light, and the light-receiving means is an array.

By using linear light and by receiving reflected light with array-shaped PD, it is possible to measure multiple locations on a straight line on the card simultaneously.

The invention described in Structure (3-21) is a displacement measurement apparatus wherein intensity of regular reflected light on a flat portion other than a convex portion or a concave portion of the card is greater than intensity of diffused light captured by the converging lens of the invention described in Structure (3-19) or (3-20).

When light is irradiated on a card, reflected light is composed of regular reflected light which is reflected in the direction at an angle for the normal line on the surface of the card, said angle being identical to that for incident light irradiated, and of diffused light.

Since the diffused light from a flat portion and that from a convex portion or a concave portion are in the same intensity in any direction ideally (actually, they are not exactly the same because of a certain extent of directivity), the diffused light from a convex portion or a concave portion enters a light-receiving means through a converging lens. On the other hand, regular reflected light from a convex portion or a concave portion does not pass through the converging lens and does not enter the light-receiving means.

In the invention, intensity of regular reflected light from a flat portion is made to be greater than that of diffused light from a convex portion or a concave portion, which make it possible to discriminate between a flat portion and a convex portion or a flat portion and a concave portion. Incidentally, the greater is the difference of intensity, the easier is the discrimination.

BRIEF DESCRIPTION OF THE DRAWINGS

FIG. 5 is a diagram illustrating the second embodiment.

FIGS. 6(a) and 6(b) are diagrams illustrating the third embodiment.

FIG. 7 is a diagram illustrating a light-receiving element in the third embodiment.

FIG. 17 is a diagram illustrating the eleventh embodiment.

DETAILED DESCRIPTION OF THE PREFERRED EMBODIMENT

Figure 1:
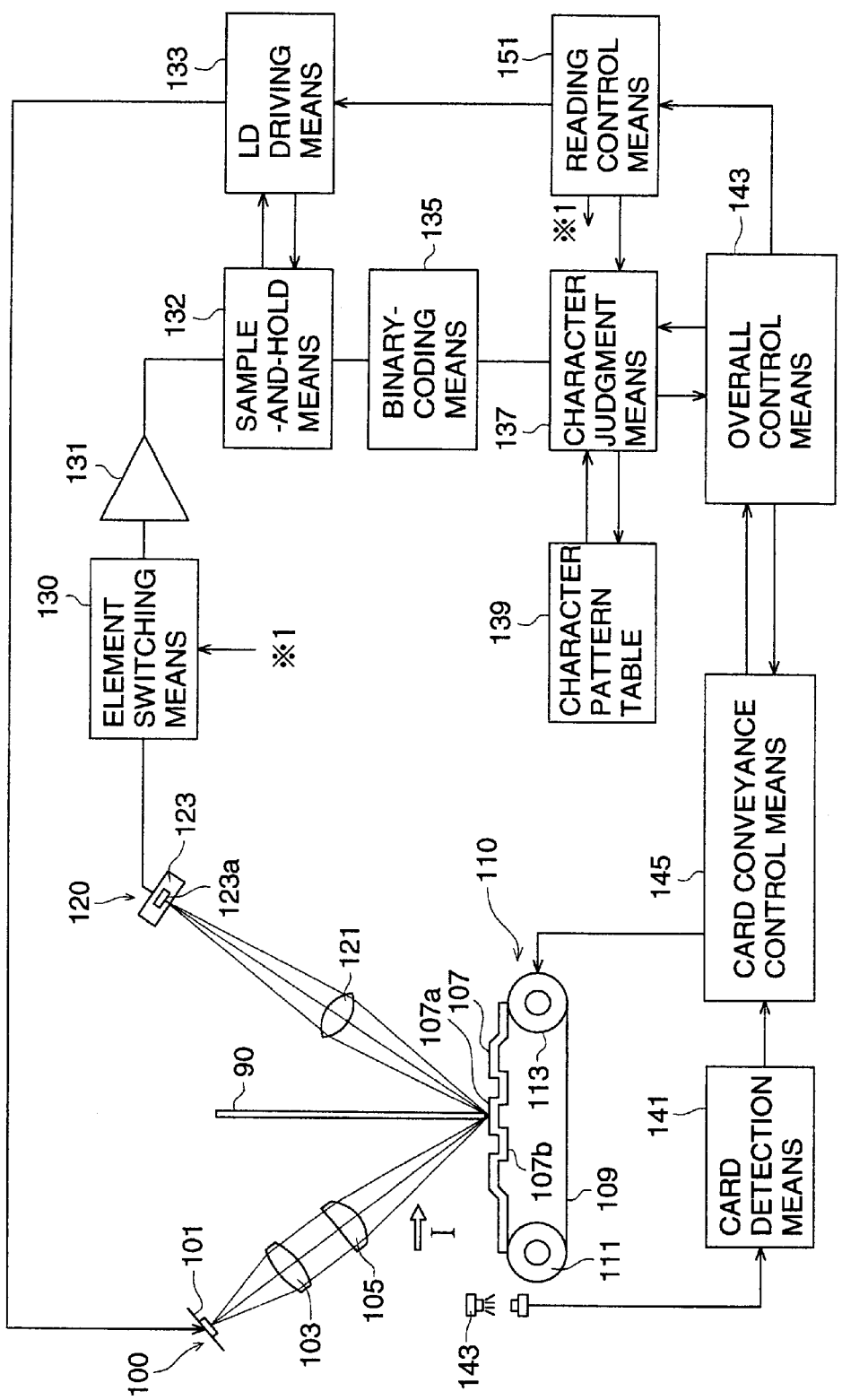
FIG. 1 is a structure diagram illustrating the first embodiment.

In the embodiment of the invention explained below, a surface on one side of the card having a character of unevenness formed actually through embossing is to be subjected to displacement measurement.

Though a card is preferable as an object (a detection object) to be inspected in the invention, the invention is not limited to the card. Further, though embossment is preferable as a concave portion and a convex portion of an object to be inspected in the invention, the invention is not limited to the embossment.

An explanation will be given as follows, as a character formed with an original flat portion of a card and with a concave portion or a convex portion (a concave portion or a convex portion for an original flat portion on the surface on one side of the card), or a character formed with a concave portion or a convex portion.

A surface displacement detection apparatus of the invention will be explained.

A surface displacement detection apparatus of the invention is one for detecting a concave portion, a convex portion or a hole portion of an object to be inspected (more preferably, detecting even an amount of displacement of a concave portion, a convex portion or a hole portion), and it has therein a light-shielding means (a light-shielding device) provided in the direction crossing the surface of an object to be inspected, a light-irradiating means (a light-irradiating device) which is provided on the one side of the light-shielding means and irradiates light on an object to be inspected, a light-receiving means (a light-receiving device) which is provided on the other side of the light-shielding means and receives at least one of the regular reflected light and diffused reflected light from the surface of an object to be inspected, and a conveyance means (a conveyor) which conveys at least one of the object to be inspected and the light-irradiating means. Incidentally, it is preferable that the light-shielding means is in the direction crossing the conveyance direction. Incidentally, "providing the light-irradiating means on one side of the light-shielding means" means that the light-irradiating means may either be provided to be in contact with the light-shielding means or be provided without being in contact with the light-shielding means.

A surface displacement detection apparatus of the invention is also considered to have a light-pickup apparatus. In this case, the light-pickup apparatus has therein a light-shielding means provided in the direction crossing the surface of an object to be inspected, a light-irradiating means which is provided on one side of the light-shielding means and irradiates light on an object to be inspected, and a light-receiving means which is provided on the other side of the light-shielding means and receives at least one of the regular reflected light and diffused reflected light from the surface of an object to be inspected.

It is preferable that the surface displacement detection apparatus has therein a pattern recognition section which recognizes a pattern on the surface of an object to be inspected from information of displacement for a concave portion, a convex portion or a hole portion of an object to be inspected. Due to the pattern recognition section thus provided, it is possible to use as an information reading apparatus which minutely reads information of an object to be inspected recorded by a concave portion, a convex portion or a hole portion. Accordingly, the surface displacement detection apparatus of an optical system can also be used as an information reading apparatus of an information recording medium.

When an object to be inspected has a flat portion and a concave portion, it is preferable that a light-irradiating means, a light-shielding means and a light-receiving means are arranged so that light reflected on the flat portion or light diffused on the flat portion is shielded by the light-shielding means, and light reflected on the concave portion or light diffused on the concave portion advances to the light-receiving means. When an object to be inspected has a flat portion and a convex portion, it is preferable that a light-irradiating means, a light-shielding means and a light-receiving means are arranged so that light reflected on the convex portion or light diffused on the convex portion is shielded by the light-shielding means, and light reflected on the flat portion or light diffused on the flat portion advances to the light-receiving means. The light-shielding means prevents at least a part of regular reflection light and diffuse reflection light on the object from being introduced into the light receiving means.

It is further preferable that the light-shielding means is movable in the direction which is almost crossing the surface of an object to be inspected, and the light-shielding means is brought into contact with an object to be inspected. Or, it is preferable that the light-shielding means forms a clearance between its end surface which faces an object to be inspected and an object to be inspected. Incidentally, as the light-shielding means, a flat plate-shaped member, a shutter, a wave-shaped plate, a notched plate or a block-shaped plate may be used. However, the light-shielding means may be not limited to these members. It may be preferable that the light-shielding means is colored black.

Further, though it is preferable that the conveyance means has a conveyance section for an object to be inspected such as a roller and a belt, the conveyance means may also have a conveyance section for a pickup apparatus which moves a light-pickup apparatus. Incidentally, it is preferable that a speed of relative movement is not less than 0.1 m/s, and it is more preferable that the speed is not less than 0.2 m/s.

It is preferable that the light-irradiating means has a light source and an optical element which irradiates light emitted from the light source on an object to be inspected. It is also preferable that the light-receiving means has a condenser lens which condenses at least one of the regular reflected light and the diffused reflected light from the surface of an object to be inspected concerning light irradiated through an optical element and a light-receiving element which receives light condensed by the condenser lens.

It is further preferable that the light-irradiating means irradiates straight-line-shaped light on an object to be inspected. In that case, the optical element preferably is a cylindrical lens. Or, it is preferable that the light-irradiating means irradiates plural spotlight beams arranged to be almost in a straight line on an object to be inspected. In that case, the optical element preferably is a micro-lens array.

When irradiating straight-line-shaped light or when irradiating plural spotlight beams arranged to be almost in a straight line, it is preferable that plural light-receiving elements are provided and these plural light-receiving elements are arranged in a straight line form, or that light-receiving elements are arranged in a straight line form and are divided into plural portions. To be more concrete, either PD divided into n (n represents integers of 2 or more) in the linear direction of linear light or in the direction in which plural spotlight beams are arranged and divided into m (m represents integers of 1 or more) in the linear direction of linear light or in the direction crossing the direction in which plural spotlight beams are arranged, or PSD array wherein n (n represents integers of 2 or more) pieces are arranged in the linear direction of linear light or in the direction in which plural spotlight beams are arranged, is especially preferable.

Incidentally, it is preferable that the surface displacement detection apparatus detects a concave portion, a convex portion or a hole portion of an object to be inspected based on the light-receiving position on a light-receiving element. It may be preferable that the displacement of the light receiving position on the light-receiving element is a positional change on the light-receiving element in accordance with an angular change of an optical axis of the light flux introduced into the light receiving element. Preferably, the displacement of the light-receiving position on the light-receiving element is displacement of the position in the direction which is in parallel with the light-receiving element. More preferably, the displacement of the light-receiving position on the light-receiving element is displacement of the position in the direction which is perpendicular to an optical axis. It is further preferable that the displacement of the light-receiving position on the light-receiving element is displacement of (one-dimensional) position on the straight line without being displacement of a position in every direction on the plane surface. By employing the structure of this kind, it is possible to obtain an apparatus which can detect inexpensively and accurately a concave portion, a convex portion or a hole portion (preferably, even an amount of displacement thereof) of an object to be inspected. Preferable reasons also include that it is easy to set dynamic range of reading signals to be broad. It is further preferable that the light-receiving element has a means to transmit linearly a change in an amount of detection or in a detection position based on changes in time as electric signals. Due to this structure, it is possible to detect a change in surface displacement caused by a change in movement of an object to be inspected, when detecting the surface displacement while conducting relative movement between an object to be inspected and light, which is preferable.

Various type of light sources can be used as a light source. LED and a halogen lamp may be used, and even a laser light source such as a laser diode emitting laser light may be used. The preferable is a laser light source having a great light converging function. When using PD or PSD as a light-receiving element, it is preferable that a wavelength of the light source is in a range of 600–1000 nm.

Incidentally, when a light source is a laser diode in the case of using an optical element having a tendency of direction in light-converging operation when irradiating linear light on an object to be inspected, it is preferable that the laser diode is provided so that the direction of a major axis of an ellipse-shaped far field pattern of the laser diode may agree with the linear direction of linear light. By employing this structure, linear light on an object to be inspected becomes thin uniformly and optical reading power is improved, because uniformity with high intensity of light is obtained and light-converging power in one direction on an optical element having a tendency in direction in the light-converging direction is improved. In addition, utilization efficiency for light is enhanced.

It is further preferable that a width of light in the scanning direction (movement direction) on an object to be inspected is smaller than that in the scanning direction for a concave portion, a convex portion or a hole portion of the object to be inspected. To be concrete, a width of light which is not greater than 0.3 mm is preferable, and that of 0.1 mm or less is more preferable. Due to this structure, it is possible to generate the condition that light hits a concave portion or a convex portion without hitting a flat portion. It is therefore possible to detect easily a convex portion, a concave portion or a flat portion, and reading accuracy for a concave portion, a convex portion or a hole portion (preferably, an amount of displacement for each of them) is improved. Incidentally, in the case of this structure, it is preferable to use a fixed illumination optical system wherein a size of light is not greater than a width of a convex portion or a concave portion even when light is hitting a convex portion or a concave portion of a card and even when light is hitting a flat portion of a card.

Further, a lens used for a condenser lens and for an optical element has only to be a lens having a light-converging power, and it may also be either a glass lens or a plastic lens. It may further be either a single convex lens Or a combination of a convex lens and a concave lens. It may further be a hologram lens, a Fresnel lens, GRIN lens and a lens of a refractive index distribution type. For the purpose of controlling aberration on a light-receiving element, an aspheric lens is preferable.

It is preferable that a lens used for a condenser lens and for an optical element is a positive lens having a small numerical aperture (NA). The reason for this is that, when a positive lens having small NA is used, a focal depth on an object to be inspected is great, and it is possible to irradiate a light flux sufficiently condensed on a light-receiving element independently of the position of an object to be inspected in the direction of an optical axis. Namely, it is possible to have sufficient room for slippage in the optical axis direction in setting an object to be inspected. To be concrete, in the case of a positive lens, it is preferable to use a lens having NA of not more than 0.2. In this case, the focal depth which makes a spot diameter having high resolving power to be 0.3 mm or less is ±0.75 mm or more, which is preferable. It is especially preferable to use a lens whose NA is not more than 0.15. In this case, the focal depth which makes a spot diameter having high resolving power to be 0.3 mm or less is ±1.0 mm or more, which is more preferable.

It is further preferable that an optical element has a lens or a member having a prescribed opening. The optical element may also have a linear light generating optical element which makes light on an object to be inspected to be a linear light by converging, or polarizing, or shielding light emitted from a light source. As a linear light generating optical element, it is preferable to have a slit or a cylindrical lens. Further, the optical element may also have a dividing section which divides light emitted from a light source into plural light fluxes. Concretely, there is given a plurality of lenses and a plate having plural-holes. Incidentally, it is preferable that light irradiated on an object to be inspected is collimated light.

It is preferable that an object to be detected by the surface displacement detection apparatus is a plane-surface-shaped object having a concave portion, a convex portion or a hole portion, and a card is especially preferable. In addition, types of the concave portion, convex portion or the hole portion are not limited in particular, and there are given an embossed article having shapes of characters and figures, a simple point or line, and a microscopic concave portion, a convex portion or a hole portion each having the maximum width of 0.3 mm or less. It may also be a combination thereof. Incidentally, it is preferable that a range of displacement in the direction of height of a concave portion, a convex portion or a hole portion of an object to be detected is 1 mm or less. The more preferable is 0.5 mm or less.

Next, an embodiment which is more concrete will be explained as follows, referring to the drawings.

(1) First Embodiment

An explanation will be given by using FIG. 1 which is a structure diagram illustrating the first embodiment.

In the drawing, there is provided light-shielding plate 90 representing a light-shielding means in the direction crossing card 107 (direction which is almost perpendicular to card 107 in this embodiment).

Light-irradiating means 100 provided on one side of the light-shielding plate 90 is composed of semiconductor laser diode (hereinafter referred to as LD) 101 representing a light source, collimator lens 103 which makes a laser beam emitted from LD 101 to be a parallel beam, and cylindrical lens 105 which condenses light made by collimator lens 103 to be a parallel beam in one direction and irradiates it on card 107 as a straight-line-shaped light.

It is arranged so that the card 107 is conveyed by conveyance means 110 composed of conveyance belt 109, driven roller 111 and driving roller 113 in the direction (direction of arrow I in the drawing) crossing the linear direction of linear light.

On the surface of the card 107, there is formed a character by flat portion 107a and concave portion 107b.

On the other side of the light-shielding plate 90, there is provided light-receiving means 120.

The light-receiving means 120 is composed of condenser lens 121 which condenses either one (diffused light in this embodiment) of a regular reflected light and a diffused light both from the surface of the card 107 and of plural array-shaped light-receiving elements (PSD in this embodiment).

Figure 2:
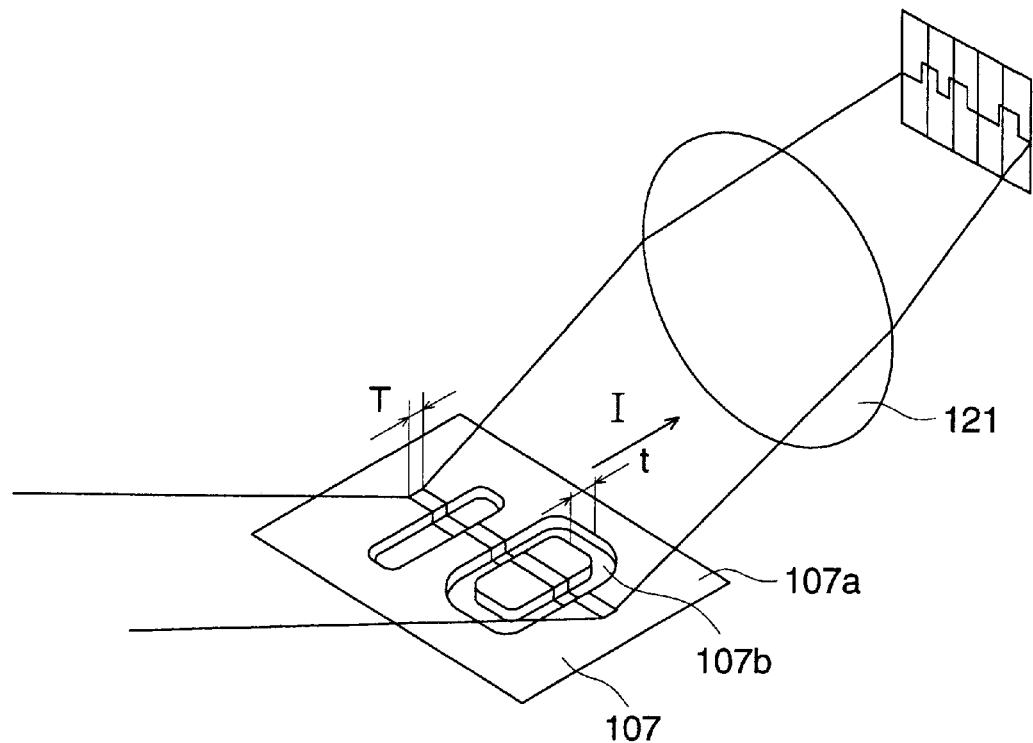
FIG. 2 is a diagram illustrating a light-receiving surface of PSD in FIG. 1.

Light-receiving surface 123a of PSD 123 is composed of PSDs in quantity of N (5 in this embodiment) arranged in the linear direction of linear light as shown in FIG. 2.

Incidentally, in the present embodiment, width (T) of a linear light is set to be smaller than minimum width (t) of concave portion 107b.

In general, a width of concave portion 107b which is to be read and is formed through embossing is about 0.8 mm, while, it is preferable that a width of a linear light is not more than 0.8 mm, and it is more preferable to be 0.1 mm or less.

In FIG. 1 again, the numeral 130 is an element switching means which switches analog signals coming from divided light-receiving surfaces 123a of PSD 123, the numeral 131 is an amplifier which amplifies analog signals of PSD 115, and the numeral 132 is a sample-and-hold means which samples signals of each PSD 123 amplified by the amplifier 131 and holds them temporarily.

The numeral 135 is a binary-coding means which binary-codes sampled analog signals coming-from the sample-and-hold means 132, and the numeral 137 is a character judgment means which discriminates a character by referring and comparing binary-coded signals and data recorded in character pattern table 139.

The numeral 141 is a card detection-means which detects whether card 107 has been conveyed or not by using photoelectric switch 143 provided on conveyance means 110, and the numeral 145 is a card conveyance control means which receives signals from the card detection means 141 and controls driving roller 113 of conveyance means 110.

The numeral 151 is a reading control means which controls LD driving means 133, element switching means 130 and character judgment means 137, while, the numeral 143 is an overall control means which controls card detection means 137, card conveyance control means 145 and reading control means 151.

Next, operations of the aforesaid structures will be explained.

When card 107 is set on conveyance means 110, photoelectric switch 143 responds, and card detection means 141 lets card conveyance control means 145 know that card 107 has been set.

The card conveyance control means 145 receives signals from the card detection means 141, and drives driving roller 113 of conveyance means 110 to convey the card 107 which has been set in the direction of arrow I.

When the card conveyance control means 145 operates, the overall control means 143 drives LD driving means 133 through reading control means 151 and makes LD 101 to be lit.

Figure 3:
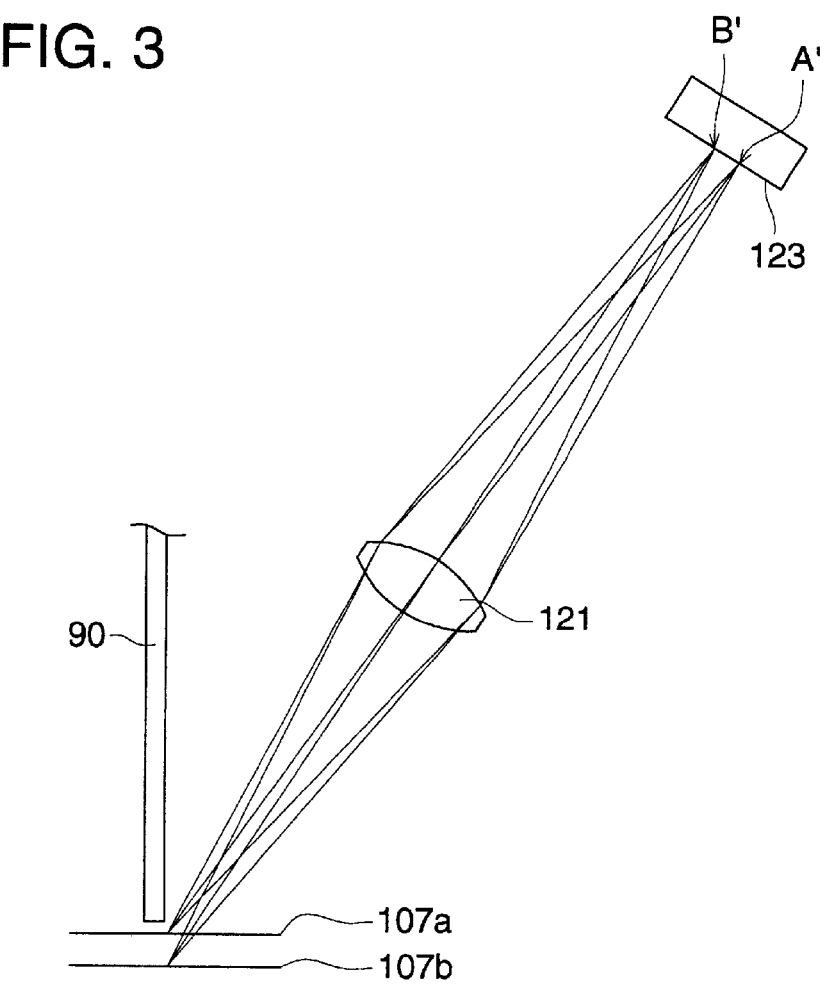
FIG. 3 is a diagram illustrating operations in FIG. 1.
Figure 4:
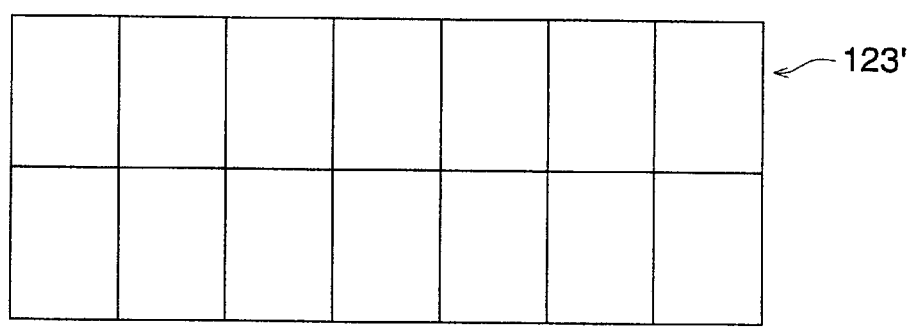
FIG. 4 is a diagram illustrating another embodiment.

As shown in FIG. 3, light reflected on flat portion 107a of card 107 among linear light irradiated on card 107 arrives at A' of light-receiving surface 123a of PSD 123, while, light reflected on concave portion 107b arrives at B' of light-receiving surface 123a of PSD 123, which means that light-receiving positions are different each other.

Therefore, light reflected on flat portion 107a is different from light reflected on concave portion 17b in terms of output from PSD 115, thus, it is possible to judge whether the portion is flat portion 107a or concave portion 107b.

Incidentally, though the explanation was given by the use of an example of a character formed by flat portion 107a and concave portion 107b in the present embodiment, light-receiving positions on light-receiving surface 123a of PSD 123 are different each other to make judgment possible even in the case of a character formed by flat portion 107a and a concave portion.

By switching each element of PSD 123 with element switching means 130, it is possible to obtain data of distribution for one-dimensional displacement in the direction of height on the surface of card 107.

Further, by conveying card 107 in the direction of arrow I by using conveyance means 110, it is possible to obtain data of distribution for two-dimensional displacement in the direction of height on the surface of card 107.

Each output signal of PSD 123 is amplified by amplifier 131, and is sampled by sample-and-hold means 132 to be preserved temporarily.

Data of distribution for displacement in the direction of height on the surface of card 107 preserved in sample-and-hold means 132 are binary-coded by binary-coding means 135, and then, character judgment means 137 conducts comparing and referring for the binary-coded data and data of character pattern table 139 to judge a character formed by concave portion 107b on card 107. The foregoing is a basic optical system.

In the aforesaid structure, when an edge portion of light-shielding means 90 is provided to be positioned in the vicinity of the surface (flat portion) of card 107 in the case of a character formed by a concave portion, a regular reflected light and a diffused light both on the flat portion are cut more by light-shielding means 90, compared with a regular reflected light and a diffused light both on concave portion 107b, and the central angle of a light flux arriving at PSD 123 is greatly changed, and a center of gravity of light entering PSD 123 is greatly changed.

It is therefore easy to discriminate between a flat portion and a concave portion, even in the case of card 107 having poor reflectance for light.

When a character is formed by a convex portion, if an edge portion of light-shielding means 90 is provided to be positioned in the vicinity of the convex portion of card 107, a regular reflected light and a diffused light both on the convex portion are cut more by light-shielding means 90, compared with a regular reflected light and a diffused light both on flat portion 107a, and the central angle of a light flux arriving at PSD 123 is greatly changed, and a center of gravity of light entering PSD 123 is greatly changed.

It is therefore easy to discriminate between a flat portion and a concave portion, even in the case of card 107 having poor reflectance for light.

By using cylindrical lens 105, cost reduction is achieved.

Further, by setting width (T) of linear light to be smaller than minimum width (t) of concave portion 107b, linear light hardly hits flat portion 107a when it is hitting concave portion 107b.

It is therefore easy to detect whether the portion is a concave portion or a convex portion, and reading accuracy for concave portion 107b is improved.

Further, though a character is judged by light diffused on card 107 in the present embodiment, a character can also be judged by regular reflected light on card 107.

In addition, PSD 123 can be replaced also by PD (photodiode) 123' divided in quantity of n (7 in the drawing) in the linear direction of linear light and divided in quantity of m (2 in the drawing) in the direction crossing the linear direction.

(2) Second Embodiment (Corresponding to Structure 3-3)

An explanation will be given by the use of FIG. 5. Incidentally, the same items as those in the first embodiment are given the same symbols, and overlapped explanation will be omitted.

FIG. 5 corresponds to a diagram obtained by viewing in the direction of arrow I in FIG. 1. In the present embodiment, micro-lens array 201 wherein convex lenses are provided in a shape of an array is used in place of a cylindrical lens.

In the aforesaid structure, when intensity distribution is broad in LD (light source) 101, intensity of an individual spot light can be adjusted by an area of each lens of micro-lens array 201, and thereby, uniform spot light beams can be irradiated.

By using micro-lens array 201, it is also possible to use a beam size method in which a diameter of a beam arriving at a light-receiving means is used for judging whether the portion is a flat portion of a card, a convex portion or a concave portion of a card.

(3) Third Embodiment (Corresponding to Structures 3-4 and 3-5)

An explanation will be given by the use of FIG. 6. Incidentally, the same items as those in the first embodiment are given the same symbols, and overlapped explanation will be omitted.

In the present embodiment, light-shielding plate 90 is arranged at the position which is almost the same as the surface of a card at which the light-shielding plate 90 almost comes in contact with the surface of the card 107, so that light reflected on flat portion 107a of card 107 is shielded by light-shielding plate 90 (see FIG. 6(a)) and only light reflected on concave portion 107b advances to light-receiving means 120 (see FIG. 6(b)).

It is preferable that an incident angle by light emerging means 100 is made to be small enough. For example, the preferable is 45° or less.

Therefore, at the light-receiving means 120, if a regular reflected light comes, it means concave portion 107b, and if a regular reflected light does not come, it means flat portion 107a, which makes it easy to discriminate between flat portion 107a and concave portion 107b, and it is possible to use array-shaped PD (photodiode) 210 wherein light-receiving element is not divided in the linear direction of linear light although it is divided in quantity of n (6 in the drawing) in the linear direction of linear light as shown in FIG. 7.

As a lens for light-converging, it is possible to use a lens having small NA, and focal depth can also be great.

Though a regular reflected light is used in the present embodiment stated above, it is also possible to use a diffused light. Compared with the regular reflected light, the diffused light is diverged uniformly at a solid angle.

When a diffused light is used, therefore, the degree of freedom for the position of a light-receiving means is enhanced, which makes it possible to discriminate a flat portion, a concave portion and a convex portion, even when a card is warped.

(4) Fourth Embodiment (Corresponding to Structure 3-8)

Figure 8:
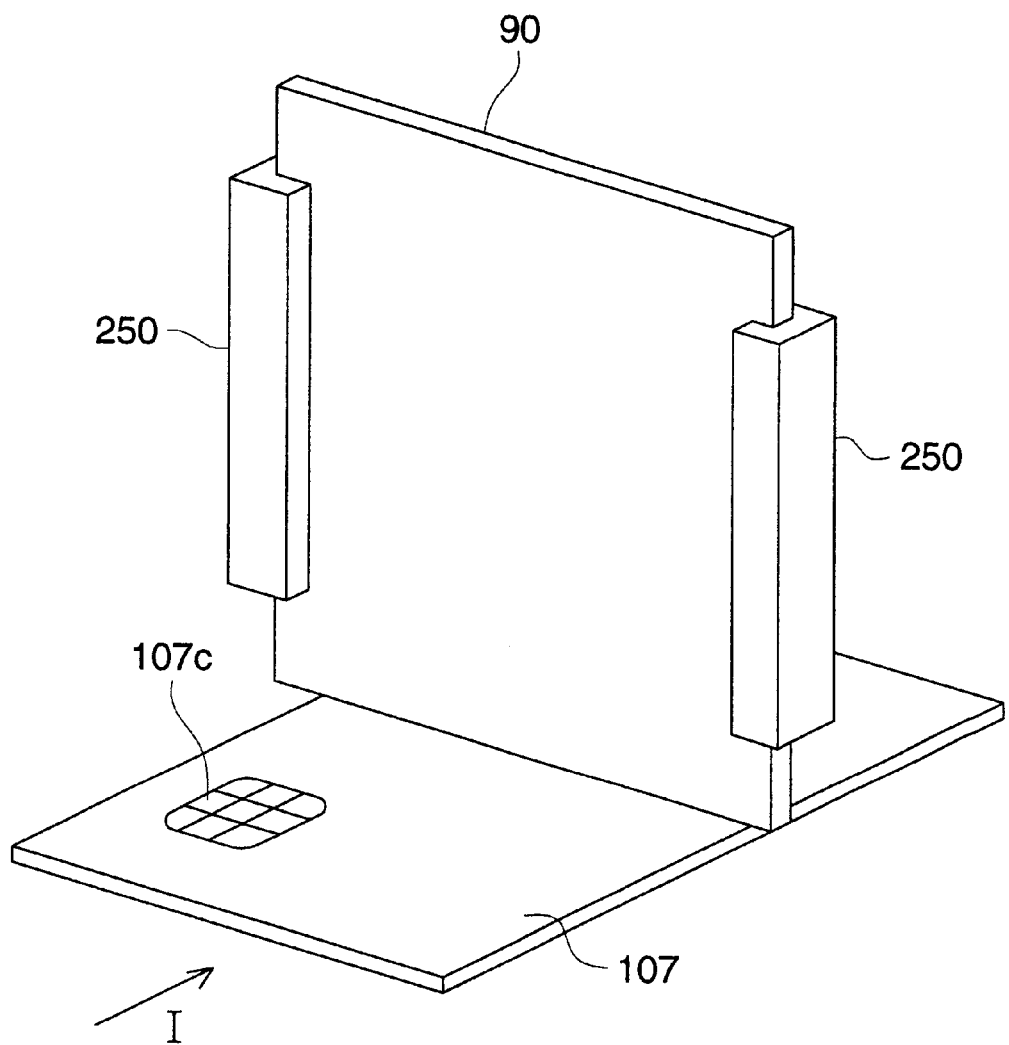
FIG. 8 is a diagram illustrating the fourth embodiment.

An explanation will be given by the use of FIG. 8. Incidentally, the same items as those in the first embodiment are given the same symbols, and overlapped explanation will be omitted.

The present embodiment is light-shielding plate 90. The light-shielding plate 90 is provided to be movable in the direction almost crossing the surface of card 107 and is arranged so that it comes in contact with the surface of card 107 by gravity.

In this case, it is preferable, from the viewpoint of better slippage on the surface of card 107, that light-shielding plate 90 is made of plastic.

In the structure stated above, reading accuracy for flat portion 107a and concave portion 107b is improved because light-shielding plate 90 moves by following the surface of card 107 and conducts light-shielding, even when card 107 is warped when the light-shielding plate 90 is brought into contact with the surface of card 107, or even when thin IC chip 107c is provided on the surface of card 107.

(5) Fifth Embodiment (Corresponding to Structure 3-9)

Figure 9:
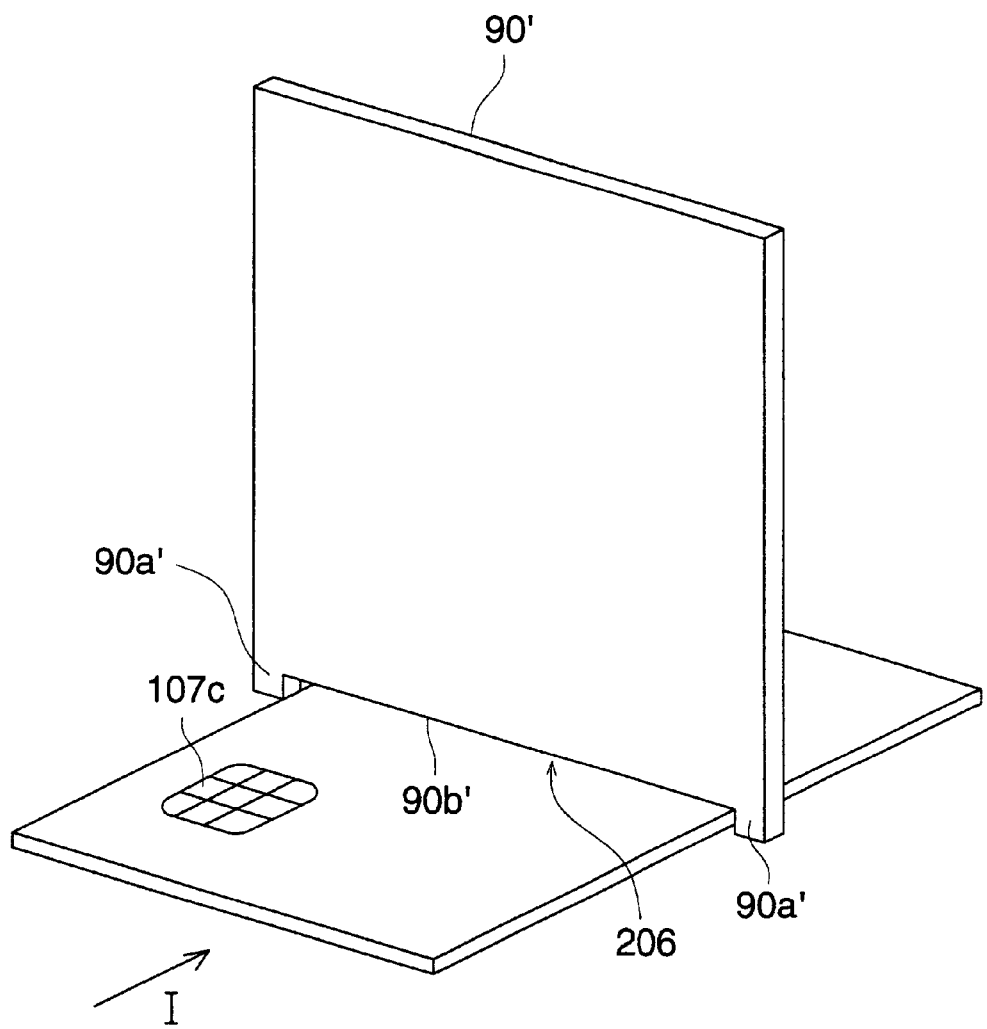
FIG. 9 is a diagram illustrating the fifth embodiment.

An explanation will be given by the use of FIG. 9. Incidentally, the same items as those in the first embodiment are given the same symbols, and overlapped explanation will be omitted.

The present embodiment is also light-shielding plate 90. Light-shielding plate 90' has contact portions 90a' which come in contact with portions other than card 107 so that clearance 260 may be formed between end surface 90b' that faces the card 107 and the surface of the card.

In the structure stated above, due to the clearance 260 formed between light-shielding plate 90' and the surface of card 107, light-shielding plate 90 does not interfere with card 107 for reading of flat portion 107a and concave portion 107b or a convex portion, even when card 107 is warped or even when thin IC chip 107c is provided on the surface of card 107.

There will be explained below another embodiment wherein discrimination between a flat portion and a concave portion, or a convex portion, or a hole portion is easy even in the case of a card having poor reflectance. Incidentally, the following embodiment may be combined with an embodiment of the invention according to circumstances, or the following embodiments may be combined with each other.

(6) Sixth Embodiment (Corresponding to Structure 3-10)

Figure 10:
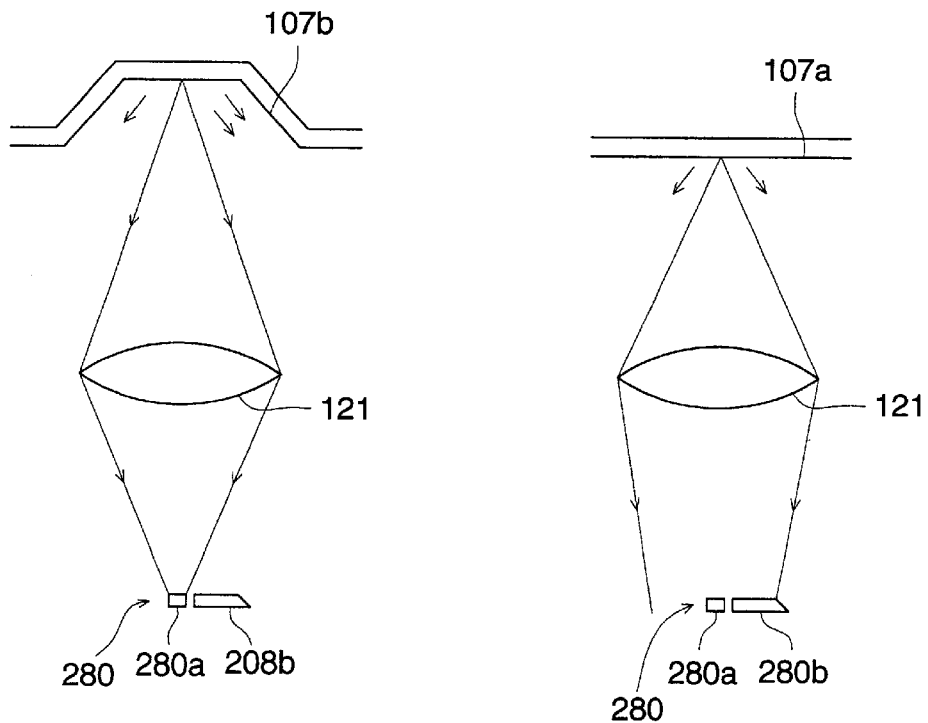
FIG. 10 is a diagram illustrating another example of the sixth embodiment.

An explanation will be given by the use of FIG. 10. Incidentally, the same items as those in the first embodiment are given the same symbols, and overlapped explanation will be omitted.

PD 280 in the present embodiment is a light-receiving element which is divided into two parts and is composed of light-receiving surfaces 280a and 280b which are asymmetrical about the direction crossing the linear direction of a linear light. By taking a value of $(A-B)/(A+B)$ when A and B represent respectively output of halved light-receiving surface 280a and that of halved light-receiving surface 280b, in an arrangement wherein light from concave portion 107b or a convex portion irradiates light-receiving surface 280a on one side and light from flat portion 107a irradiates light-receiving surfaces 280a and 280b on both sides, it is possible to obtain signals which are independent of intensity of light, and thereby to read accurately a character formed by a concave portion or a convex portion even when the reflectance on the surface of card 107 for light is lowered.

Incidentally, in the present embodiment, it is also possible to arrange so that light from concave portion 107b or from concave portion a irradiates light-receiving surfaces 280a and 280b on both sides and light from flat portion 107a irradiates light-receiving surfaces 280a on one side.

Further, sensitivity is more enhanced by making division of a light-receiving surface to be asymmetric.

Figure 11:
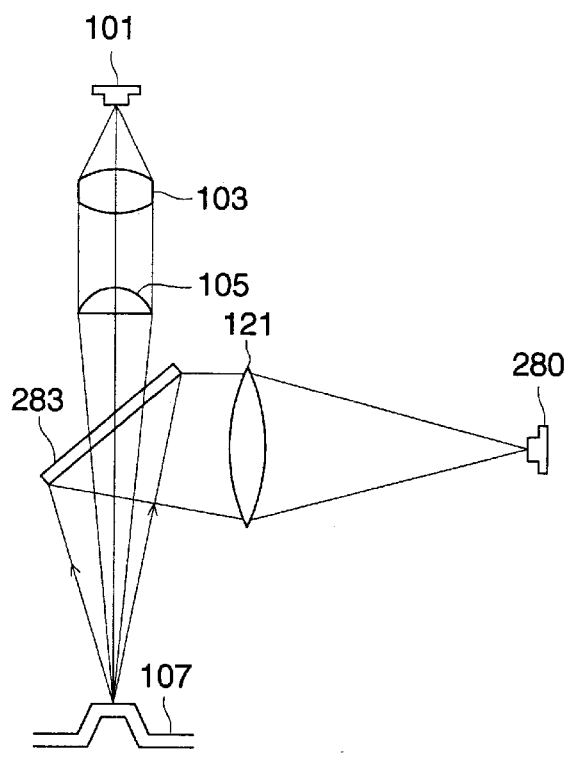
FIG. 11 is a diagram illustrating another embodiment.

Incidentally, the invention is not limited to the embodiment stated above. For example, it is also possible to employ a retro-optical system wherein half mirror 283 is used and an optical path for a light-irradiating means and that for a light-receiving means are partially used in common, as shown in FIG. 11.

(7) Seventh Embodiment (Corresponding to Structure 3-11)

Figure 12:
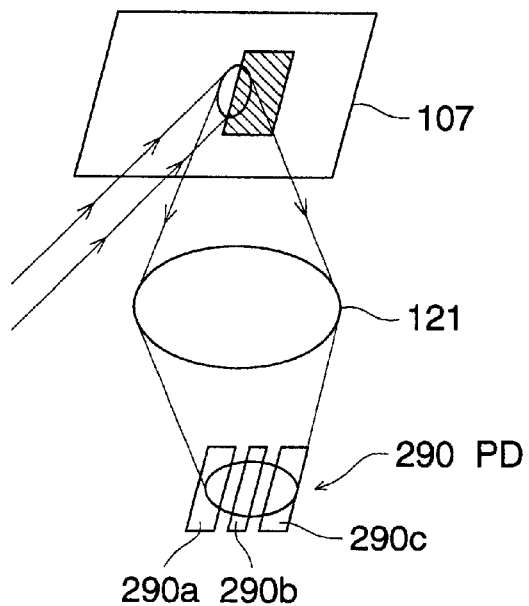
FIGS. 12(a) and 12(b) are diagrams illustrating the seventh embodiment.
Figure 12:
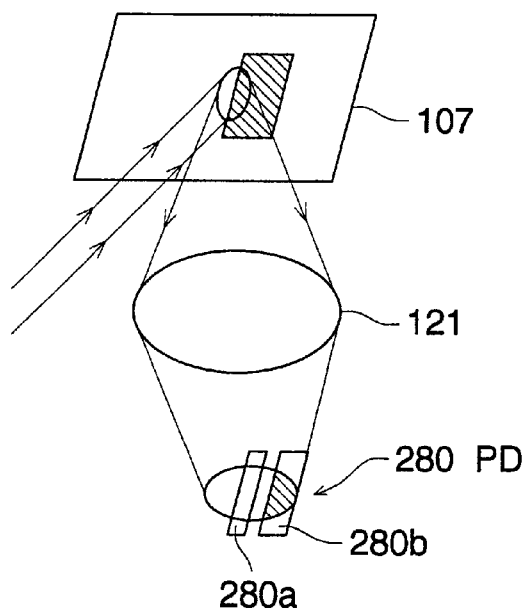

An explanation will be given by the use of FIG. 12. Incidentally, the same items as those in the first embodiment are given the same symbols, and overlapped explanation will be omitted.

As shown in FIG. 12(a), PD 290 in the present embodiment has a light-receiving surface divided into three light-receiving surfaces 290a, 290b and 290c.

When each of A, B and C represents each of output of light-receiving surfaces 290a, 290b and 290c, if a value of $((A+C)-B)/(A+B+C)$ is smaller than a prescribed value, a flat portion is identified, while, when if it is not less than a prescribed value, concave portion 107b or a convex portion is identified.

In the aforesaid structure, when two portions each having different reflectance (for example, a black portion and a white portion shown in FIGS. 12(a) and (b)) are formed, through printing or the like, on flat portion 107a of card 107, if asymmetric and halved PD 280 shown in FIG. 12(b) is used, a value of $(A-B)/(A+B)$ is made to grow greater to develop a possibility that even flat portion 107a is misjudged to be convex portion 107b or a concave portion. However, when PD 290 on which a light-receiving surface is divided into three parts is used, it is possible to make misjudgment to be hard to take place, by taking a value of $((A+C)-B)/(A+B+C)$ under the condition that each of A, B and C represents output of each light-receiving surface.

(8) Eighth Embodiment (Corresponding to Structure 3-12)

An explanation will be given by the use of FIG. 13. Incidentally, the same items as those in the sixth and seventh embodiments are given the same symbols, and overlapped explanation will be omitted.

In the present embodiment, PD 290 which is divided into three parts is used in a retro-optical system shown in FIG. 11, and light-shielding plate 300 which divides a parallel light flux into two light fluxes is further provided between collimator lens 103 and cylindrical lens 105.

In the structure mentioned above, an arrangement is made so that two light fluxes may agree with each other in terms of position on either one between flat portion 107a and concave portion 107b or between flat portion 107a and a convex portion, and two light fluxes may be separated from each other on the other.

Therefore, by using a light-receiving element whose light-receiving surface is divided into two or three parts, it is possible to discriminate between flat portion 107a and concave portion 107b or a convex portion.

In particular, when PD 290 having a light-receiving surface divided into three parts is used as in the present embodiment, it is possible to detect with better sensitivity.

By making a value of $(A+C)$ to be constant by the use of APC without conducting division of $((A+C)-B)/(A+B+C)$, it is possible to discriminate between a flat portion and a concave portion or between a flat portion and a convex portion in excellent sensitivity.

In addition, an influence by a pattern of black and white parts of a card is less.

Figures 13, 14:
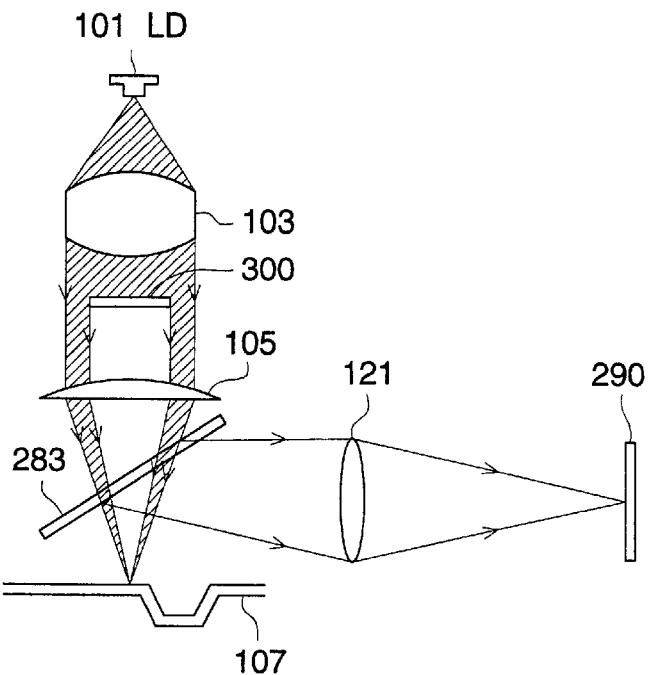
FIG. 13 is a diagram illustrating the eighth embodiment.
FIG. 14 is a diagram illustrating an effect.

As shown in FIG. 14, when there is a striped pattern having different reflectance on concave portion 107a or on a convex portion of card 107, in the seventh embodiment, light is sometimes concentrated on middle light-receiving surface 290b of PD 290, and an occasion to misjudge to be flat portion 107a is also considered.

In the present embodiment, however, light reflected on concave portion 107a or on a convex portion is divided into two light fluxes, and therefore, they enter respectively light-receiving surfaces 290a and 290c, thus, judgment can be made to the concave portion 107a or the convex portion.

A preferable optical system in the present embodiment is a telecentric optical system wherein a distance of a reading optical system is proportional to a distance between two beams of light for light-receiving.

(9) Ninth Embodiment (Corresponding to Structure 13)

Figure 15:
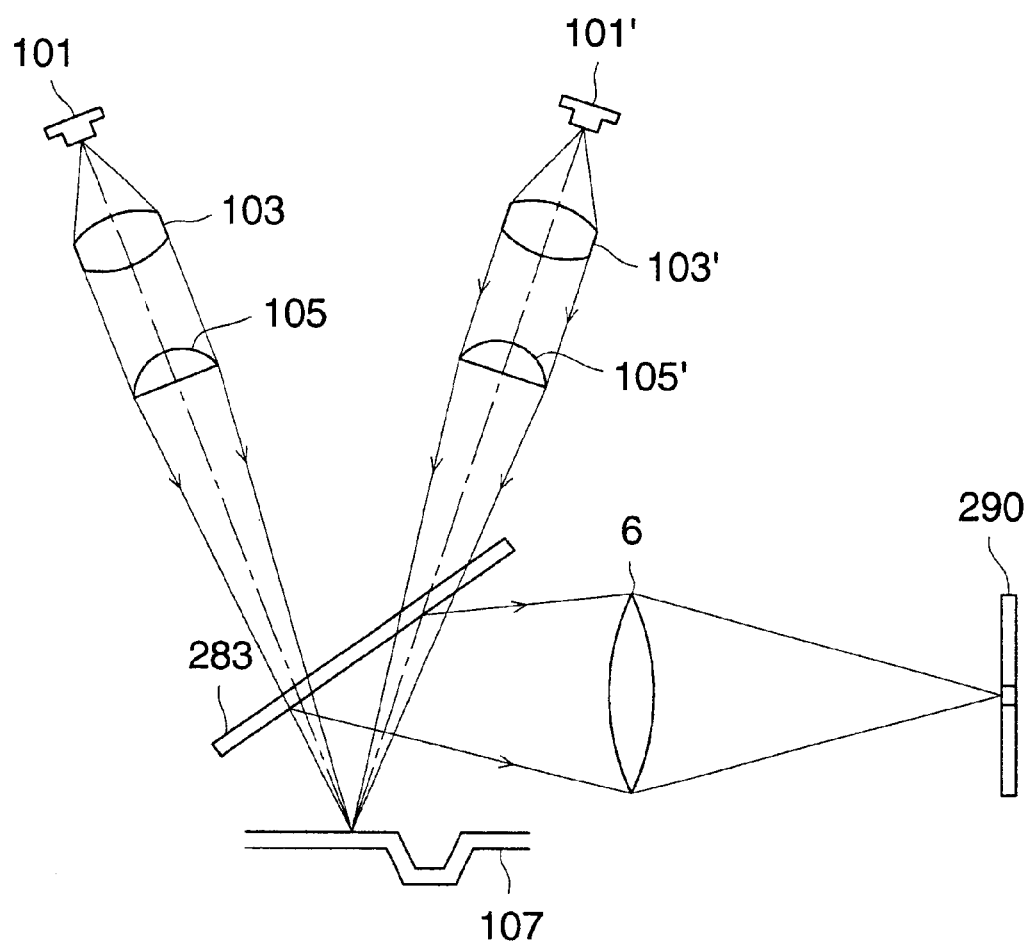
FIG. 15 is a diagram illustrating the ninth embodiment.

An explanation will be given by the use of FIG. 15. Incidentally, the same items as those in the eighth embodiment are given the same symbols, and overlapped explanation will be omitted.

There are provided two light-irradiating means in the present embodiment. Namely, they are a light-irradiating means composed of LD 101, collimator lens 103 and cylindrical lens 105 and a light-irradiating means composed of LD 101', collimator lens 103' and cylindrical lens 105'.

In the structure mentioned above, an arrangement is made so that two light fluxes may agree with each other in terms of position on either one between flat portion 107a and concave portion 107b or between flat portion 107a and a convex portion, and two light fluxes may be separated from each other on the other.

Therefore, by using a light-receiving element whose light-receiving surface is divided into two or three parts, it is possible to discriminate between flat portion 107a and concave portion 107b or a convex portion, in the same way as in the eighth embodiment.

When realizing a telecentric optical system by using one light source as in the eighth embodiment, its cost is high. However, in the present embodiment, LDs 101 and 101'which represent a light source are provided, and thereby, it is possible to realize an optical system which is inexpensive and precise and shows behaviors which look like those of a telecentric optical system.

(10) Tenth Embodiment (Corresponding to Structure 3-14)

Figure 16:
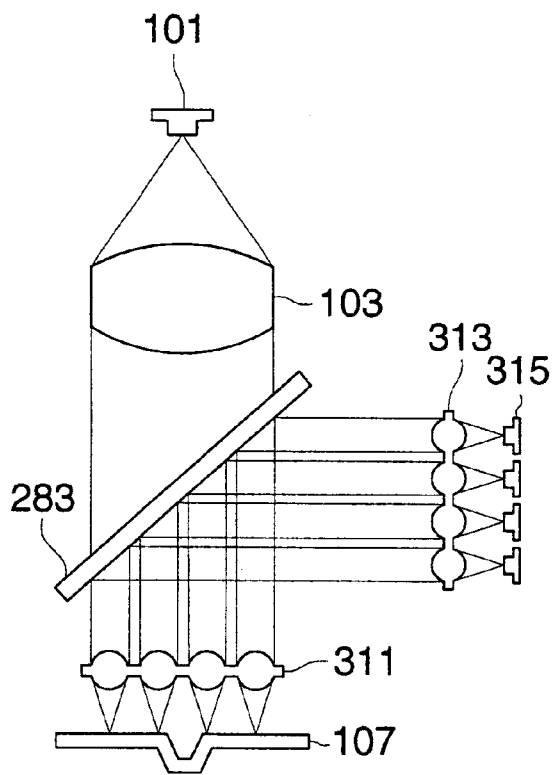
FIGS. 16(a) and 16(b) are diagrams illustrating the tenth embodiment.
Figure 16:
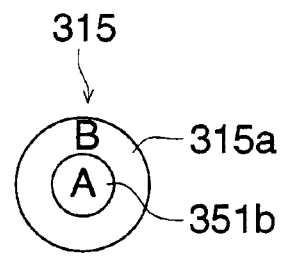

An explanation will be given by the use of FIG. 16. Incidentally, the same items as those in the eighth embodiment are given the same symbols, and overlapped explanation will be omitted.

As shown in FIG. 16(a), light which is made to be a parallel light flux by collimator lens 103 and is transmitted through half mirror 283 projects, on card 107, spot beams arranged to be almost in a straight line, through micro-lens array 311.

Light reflected on card 107 is reflected on half mirror 283 through micro-lens array 311, and then, is condensed by micro-lens array 313 to enter PD 315.

PD 315 in the present embodiment is PD divided into two parts wherein light-receiving surface 315a and light-receiving surface 315b are formed separately to be in concentric circles as shown in FIG. 16(b).

Output of light-receiving surface 315a and that of light-receiving surface 315b on PD 315 are detected by a beam size method ((A−B)/(A+B)).

By detecting through a beam size method in the structure stated above, light for light-receiving is changed greatly, and discrimination between flat portion 107a and concave portion 107b or a convex portion of card 107 is easy, even in the case of a card having poor reflectance for light.

(11) Eleventh Embodiment (Corresponding to Structures 3-15, 3-16 and 3-17)

An explanation will be given by the use of FIGS. 17 and 18. Incidentally, the same items as those in the first embodiment are given the same symbols, and overlapped explanation will be omitted.

The numeral 400 is a contact means having a plurality of contact type displacement detection sensors 401 which are provided to come into contact with a card and are arranged almost in a shape of a straight line.

Incidentally, arrangement of the contact type displacement detection sensors 401 is in the direction crossing the conveyance direction for card 107 by conveyance means 110.

Figure 18A:
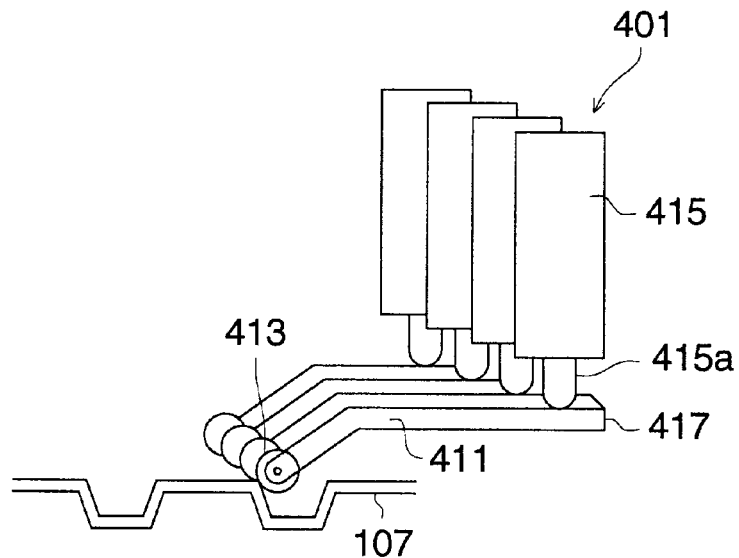
FIGS. 18(a) and 18(b) are diagrams illustrating a contact type displacement detection sensor in FIG. 17

With regard to the contact type displacement detection sensor of the present embodiment, arm 417 is supported rotatably by central shaft 411, and roller 413 which rotates on card 107 is attached on an end portion on one side of the arm 417, and contact 415a of position sensor 415 is capable of touching an end portion on the other side of the arm 417, as shown in FIG. 18(a).

In FIG. 17 again, when card 107 is set on conveyance means 110, photoelectric switch 143 responds and card detection means 141 lets card conveyance control means 145 know that the card 107 has been set.

The card conveyance control means 145 receives signals from the card detection means 141, and drives driving roller 113 of conveyance means 110 to convey the set card 107 in the direction of arrow I.

When the card 107 is conveyed in the direction of arrow I, contact type displacement detection sensor 401 of contact means 400 comes in contact with the surface of the card 107 as is understood from FIG. 18(a).

When roller 413 drops in concave portion 107b of the card 107, the arm 417 turns on shaft 411 and presses contact 415a of position sensor 415.

Therefore, a position of contact 415a corresponding to the roller 413 positioned on flat portion 107a of the card is different from that of contact 415a corresponding to the roller 413 positioned on concave portion 107b, and this difference causes a change in resistance values, and output of position sensor 415 varies depending on the resistance value, thus, the difference of output makes it possible to discriminate between flat portion 107a and concave portion 107b.

Incidentally, though an explanation has been given with an example of a character formed by flat portion 107a and concave portion 107b in the present embodiment, it is also possible to discriminate based on flat portion 107a and a convex portion, because output of position sensor 415 also varies depending them.

By taking in output of each position sensor 415, one-dimensional displacement distribution data in the direction of height on the surface of card 107 can be obtained.

Further, by conveying card 107 in the direction of arrow I by the use of conveyance means 110, two-dimensional displacement distribution data in the direction of height on the surface of card 107 can be obtained.

Each output signal of position sensor 415 is amplified by amplifier 131, then, is sampled by sample-and-hold means 132, and is stored temporarily.

Displacement distribution data in the direction of height on the surface of card 107 stored in sample-and-hold means 132 are binary-coded by binary-coding means 135, and character judgment means 137 compares the binary-coded data with data of character pattern table 139 and refers them to conduct judgment of a character formed by concave portion 107b on card 107.

In the structure stated above, flat portion 107a and concave portion 107b or a convex portion on card 107 are directly detected mechanically, which makes it easy to discriminate between a flat portion and a concave portion or a convex portion, without being affected by a factor of reflectance as in detection using light.

Further, for card 107 having poor flatness because of a warp, discrimination between a flat portion and a concave portion or a concave portion is easy.

Figure 18B:
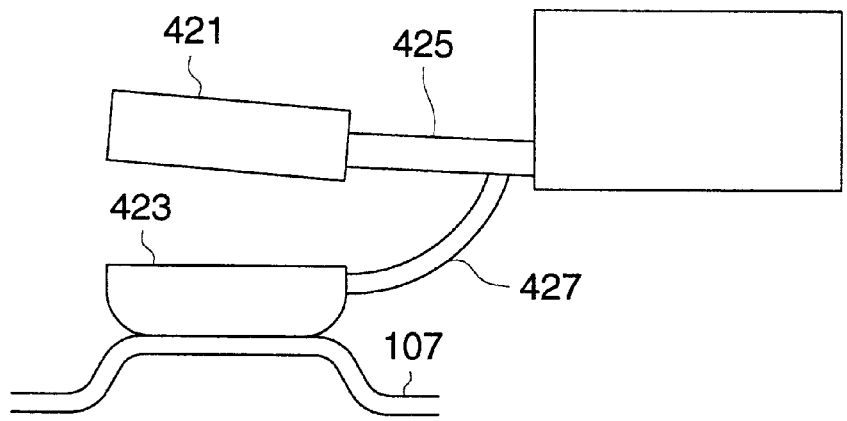

Incidentally, the invention is not limited to the embodiment stated above. Though an example of using position sensor 415 as contact type displacement detection sensor 401 has been explained in the embodiment stated above, even a linear encoder can be used, and further, it is possible to use contact type displacement detection sensor 401 wherein two electrodes 421 and 423 are provided to face each other as shown in FIG. 18(b), and the electrode 421 on one side is supported by supporting plate 425 having high rigidity, while, the electrode 423 on the other side is supported by supporting plate (flexible cord) 427 having elasticity and is brought into contact with the surface of card 107, thus, electrostatic capacity between the electrode 421 and the electrode 423 generated when the electrode 423 touches flat portion 107*a* is different from that generated when the electrode 423 touches concave portion 107*b*, which makes output to be varied.

(12) Twelfth Embodiment

A surface displacement detection apparatus of the present embodiment has a plurality of contact type displacement detection sensors. The plural contact type displacement detection sensors are arranged to be in a two-dimensional form, and when the plural contact type displacement detection sensors come into contact with an object to be inspected, a concave portion, a convex portion or a hole portion is detected. Incidentally, plural contact type displacement detection sensors may be a multi-divided contact type displacement detection sensor.

The structure mentioned above makes it easy to discriminate between a flat portion and a concave portion, or between a flat portion and a convex portion, or between a flat portion and a hole portion, even for a card having poor reflectance for light. Due to a contact means which is provided to be brought into contact with an object to be inspected on which a concave portion, a convex portion or a hole portion is formed, and has plural contact type displacement detection sensors arranged in a two-dimensional form on at least a portion where a concave portion, a convex portion or a hole portion is formed, it is possible to conduct detection at a time, which makes a conveyance means conveying at least one of an object to be inspected and a contact means to be unnecessary.

Incidentally, as a concrete example of the contact type displacement detection sensor, there are given a switch which detects whether it is in contact with an object to be inspected or not by means of ON and OFF, a sensor which recognizes a concave portion, a convex portion or a hole portion of an object to be inspected by means of a change in the value of resistance, a sensor which recognizes a concave portion, a convex portion or a hole portion of an object to be inspected by means of a change in electrostatic capacity, and a linear encoder. The sensor may be a sensor utilizing an electrical characteristic value other than the resistance value and an electrostatic capacity.

As a sensor to recognize a concave portion, a convex portion or a hole portion of an object to be inspected by means a change in the value of resistance, there may be given an embodiment wherein a contact moves in accordance with a concave portion, a convex portion or a hole portion of an object to be inspected, and a value of resistance is changed depending on the position of the contact, and output of the sensor varies depending on the value of resistance. As a sensor which recognizes a concave portion, a convex portion or a hole portion of an object to be inspected by means of a change in electrostatic capacity, there may be given an embodiment wherein two electrodes are provided to face each other, and the electrode on one side is supported by a supporting plate having high rigidity, while, the electrode on the other side is supported by a supporting plate having elasticity and is brought into contact with the surface of a card, thus, electrostatic capacity generated between two electrodes varies between a flat portion and a concave portion, which makes output to be varied. In the case of detecting by the change in electrostatic capacity, the sensor may be located in the vicinity of the object without contacting it.

Though the surface displacement detection apparatus has only to detect a concave portion, a convex portion or a hole portion, it is more preferable that it detects an amount of displacement for a concave portion, a convex portion or a hole portion. It is further preferable that the surface displacement detection apparatus has a pattern recognition section which recognizes a pattern on the surface of an object to be inspected based on information of a displacement of a concave portion, a convex portion or a hole portion of an object to be inspected. The surface displacement detection apparatus having therein this pattern recognition can be used as an information reading apparatus which minutely reads information of an object to be inspected on which a concave portion, a convex portion or a hole portion is recorded. Therefore, the surface displacement detection apparatus can also be used as an information reading apparatus for information recording media.

It is preferable that an object to be inspected which is detected by the surface displacement detection apparatus is a flat-shaped object having thereon a concave portion, a convex portion or a hole portion, and it is more preferable that it is a card. Types of a concave portion, a convex portion or a hole portion are not limited in particular, and there may be given an embossed object having a shape of a character or a figure, a mere point or line, and a microscopic concave portion, convex portion or hole portion having the maximum width of not more than 0.3 mm. A combination of the foregoing is also acceptable. Incidentally, it is preferable that a range of displacement in the direction of height for a concave portion, a convex portion or a hole portion of an object to be inspected which is detected is not more than 1 mm. The more preferable is 0.5 mm or less.

Further, it is preferable that a width of each contact type displacement detection sensor is smaller than that of a concave portion, a convex portion or a hole portion of an object to be inspected. To be concrete, a width of each contact type displacement detection sensor which is not more than 0.3 mm is preferable, and a width of not more than 0.1 mm is more preferable. Due to this structure, it is possible to prevent that a concave portion can not be detected because a contact type displacement detection touches a flat portion surrounding the concave portion, thereby, detection of a concave portion, a convex portion or a hole portion of an object to be inspected can be conducted more accurately, and reading accuracy is improved.

Next, more concrete embodiment will be explained as follows, referring to the drawings.

Figure 19:
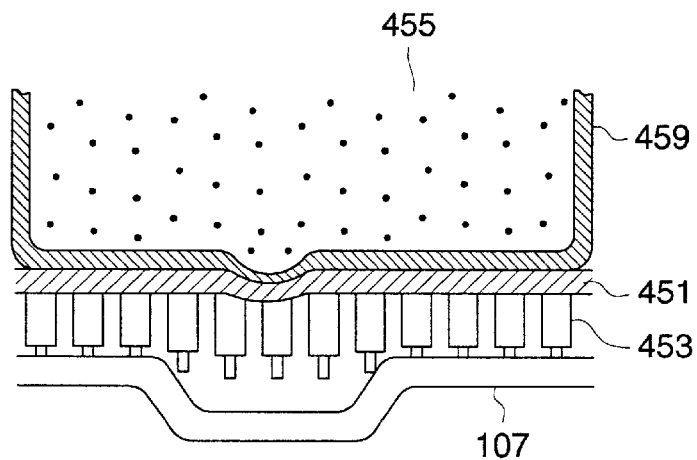
FIG. 19 is a diagram illustrating the twelfth embodiment.
Figure 26:
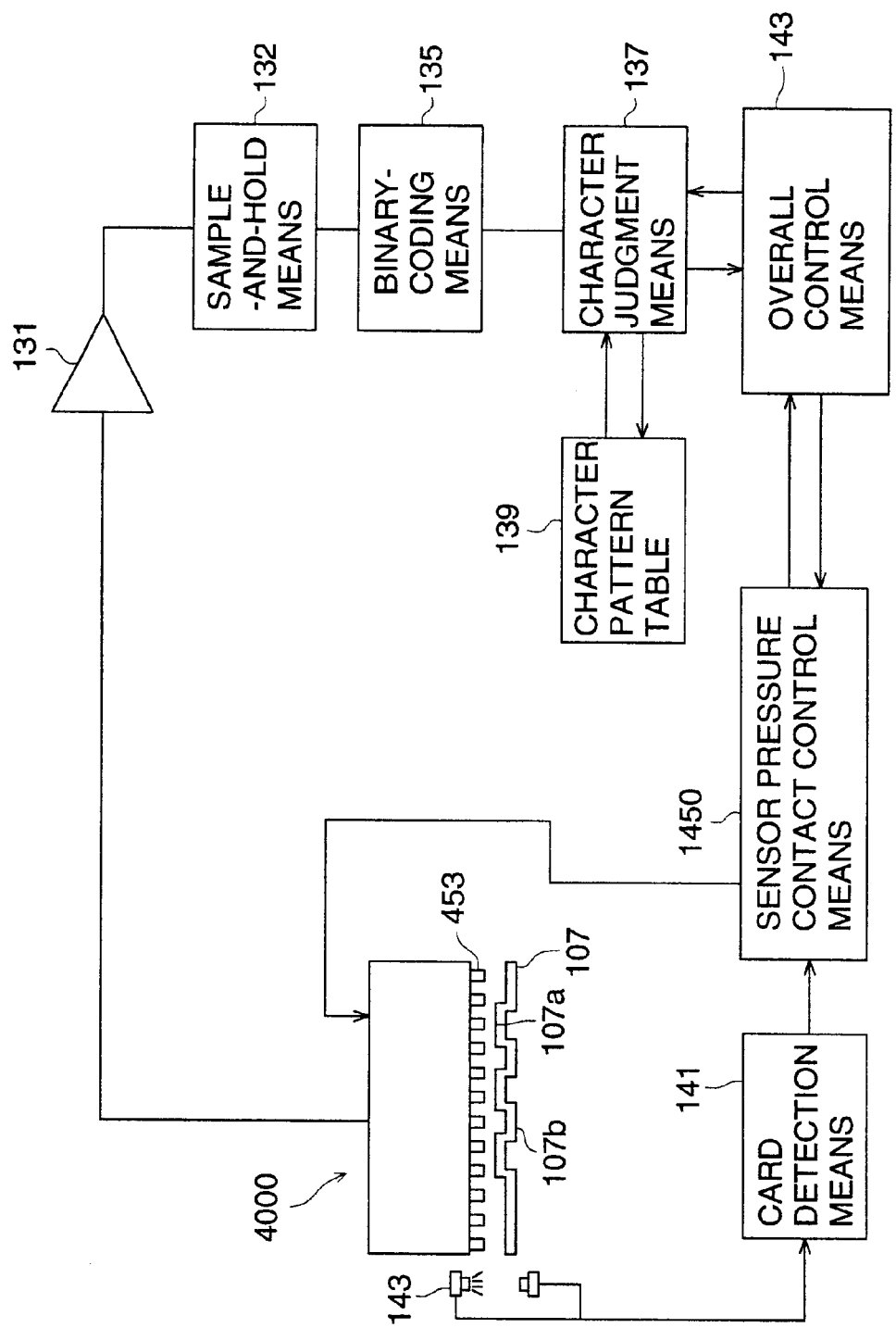
FIG. 26 is a diagram to explain an embodiment using a plurality of contact type displacement detection sensors.

FIGS. 19 and 26 will be used for explanation. The numeral 4000 is a contact means which can move in the vertical direction so that it may come into contact with a card. The contact means 4000 has a plurality of contact type displacement detection sensors 453.

When card 107 is set after passing through photoelectric switch 143, the photoelectric switch 143 responds, and card detection means 141 notifies that card 107 has been set.

Sensor pressure contact control means 1450 receives signals from card detection means 141, then, operates a contact means (not shown) which moves a contact means in the vertical direction, and makes plural contact type displacement detection sensors 453 arranged in a two-dimensional form to touch card 107. Incidentally, the contact means does not need to move in the vertical direction, and it is also possible to make a card to touch a contact means, or to make only contact type displacement detection sensor to touch the card.

As shown in FIG. 19, the contact means is one wherein microscopic switches 453 representing plural contact type displacement detection sensors which come into contact with card 107 are arranged in a two-dimensional form on the lower surface (surface on one side) of flexible base board 451, and the upper surface (surface on the other side) of the flexible base board 451 is pressed by air bag 459 filled with compressed air 455 through uniform pressure.

In the aforesaid structure, when card 107 is composed of flat portion 107*a* and concave portion 107*b*, microscopic switches 453 on flat portion 107*a* of card 107 are turned on and microscopic switches 453 on concave portion 107*b* are turned off.

When card 107 is composed of flat portion 107*a* and a convex portion, microscopic switches 453 on flat portion 107*a* of card 107 are turned off, and microscopic switches 453 for the convex portion are turned on.

By taking in output of each microscopic switch (contact type displacement detection sensor) 453, it is possible to obtain two-dimensional displacement distribution data in the direction of height on the surface of card 107 at a time.

Each output signal of each microscopic switch (contact type displacement detection sensor) 453 is amplified by amplifier 131, and then is sampled by sample-and-hold means 132 to be preserved temporarily. Displacement distribution data in the direction of height on the surface of card 107 preserved in the sample-and-hold means 132 are binary-coded by binary-coding means 135, then, character judgment means 137 compares the binary-coded data with data in character pattern table 139 and refers to them so that a character formed by concave portion 107*b* on card 107 is judged.

By processing these two-dimensional data, it is easy to discriminate between a flat portion and a concave portion, or between a flat portion and a convex portion, or between a flat portion and a hole portion, even in the case of a card having poor reflectance for light. Further, even in the case of a card having poor flatness because of a warp, it is easy to discriminate between a flat portion and a concave portion, or between a flat portion and a convex portion, or between a flat portion and a hole portion. In addition, two-dimensional detection for a character composed of a concave portion, a convex portion and a hole portion can be conducted at a time, and a conveyance means to convey a card and a contact means can be made unnecessary.

Incidentally, as a sensor pressure contact control means, an overall control means and a character judgment means, it is possible to use CPI, IC, custom IC, DSP and LSI.

(13) Thirteenth Embodiment (Corresponding to Structures 3-19, 3-20 and 3-21)

Figure 20:
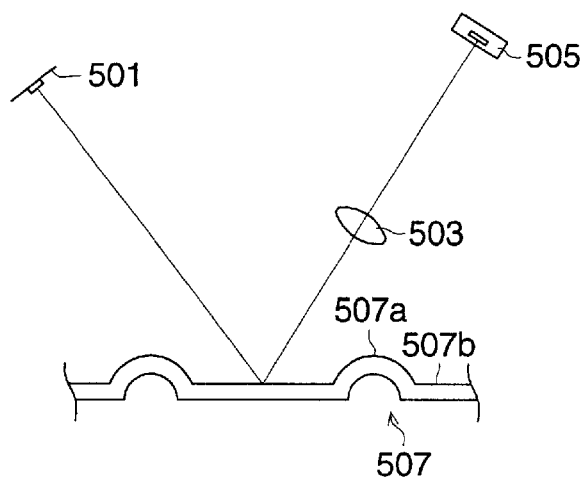
FIG. 20 is a diagram illustrating the thirteenth embodiment.

An explanation will be given by the use of FIG. 20.

In the drawing, convex portions 57*a* are formed on card 507.

Though the concrete structure of light-irradiating means 501 is omitted on the drawing, a linear light which has directivity and extends in the direction perpendicular to the page space is irradiated on card 507, in the same way as in light-irradiating means 100, for example, in the first embodiment. A regular reflected light reflected on flat portion 507*b* of card 507 is condensed by condenser lens 503 and enters array-shaped PD 505 representing a light-receiving means.

With regard to judgment, a portion where output of the light-receiving means is lowered is judged to be a concave portion of a convex portion.

The array-shaped PD 505 is provided at the position which is conjugate with the surface of card 507 through condenser lens 503.

Figure 21:
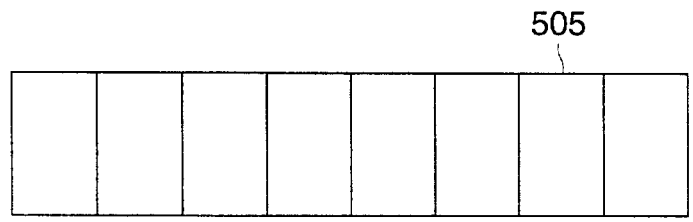
FIG. 21 is a diagram illustrating an array-shaped PD in FIG. 20.

A light-receiving surface of the array-shaped PD 505 is divided in quantity of n (divided into 7 in the drawing) in the linear direction of linear light, as shown in FIG. 21.

Figure 22:
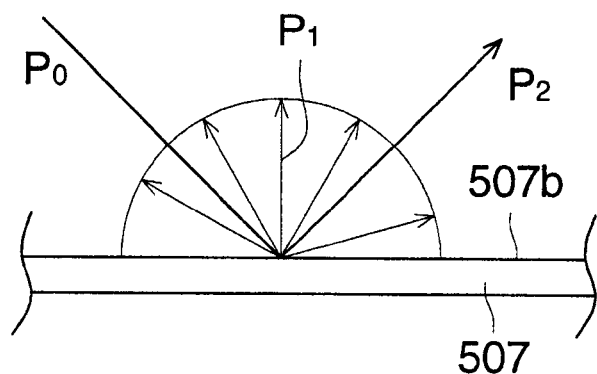
FIGS. 22(a) and 22(b) are diagrams illustrating reflection on the card in FIG. 20.
Figure 22:
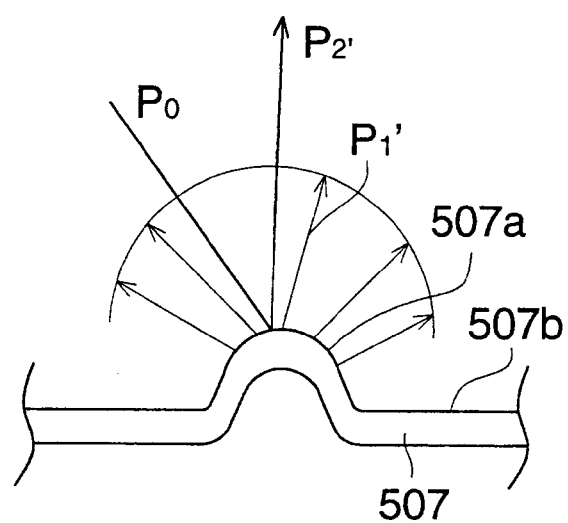
Figure 23:
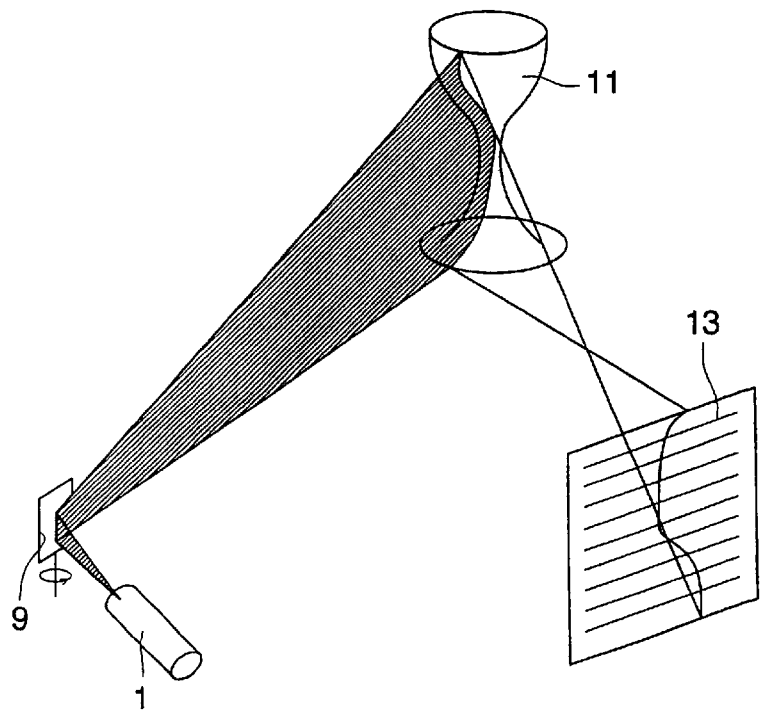
FIG. 23 is a diagram illustrating an example in the prior art.
Figure 24:
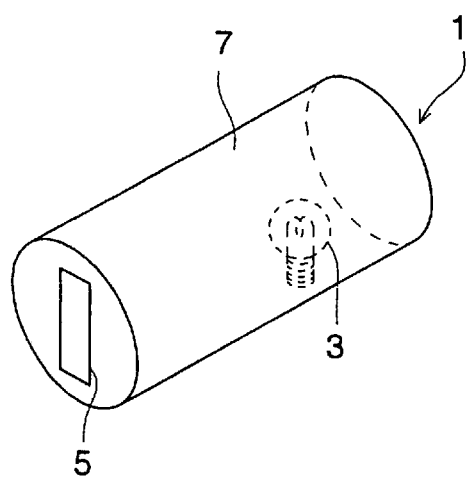
FIG. 24 is a diagram illustrating a linear light source in FIG. 23.
Figure 25:
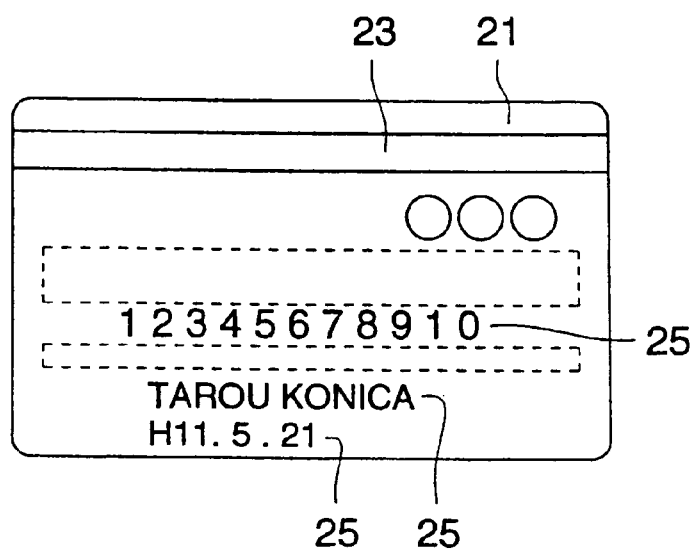
FIG. 25 is a diagram illustrating a card.

Under this structure, light irradiated on card 107 turns into one shown in FIG. 22.

Namely, as shown in FIG. 22(*a*), light reflected on convex portion 507*a* of card 507 is divided into diffused light P1 which is diffused constantly and regular reflected light P2.

As shown in FIG. 22(*b*), light reflected on convex portion 507*a* of card 507 is divided into diffused light P1' which is diffused constantly and regular reflected light P2' which advances in the direction different from that of regular reflected light P1 reflected on flat portion 507*b*.

Therefore, in the present embodiment, light which is condensed by condenser lens 503 and enters array-shaped PD 505 is a part of regular reflected light P2 and diffused light P1 in the case of light reflected on flat portion 507*b*, while, it is a part of diffused light P1' in the case of light reflected on convex portion 507*a*.

Therefore, when relationship of an amount of light is represented by P2>P1', it is possible to discriminate convex portion 507*a* on a card.

Incidentally, in the present embodiment, even when the surface of card 507 is tilted, if condenser lens 503 has an area of certain extent, card 507 and array-shaped PD 505 are in the conjugate relation because of image combination relationship. Therefore, the regular reflected light enters array-shaped PD 505.

Under the assumption that a distance from card 507 to condenser lens 503 is represented by R, an effective area (an area of an optical surface projected on the plane perpendicular to an optical axis) of condenser lens 503 is represented by S, diffusivity on card 507 is represented by γ1, and an amount of each light is represented by Pn, the following expression holds.

$$P_1 = \frac{S}{\pi R^2} \gamma_1 P_0$$

Further, when regular reflectance on card 507 is represented by γ2, the following expression holds.

$$P2 = \gamma 2 P0 \qquad (2)$$

Therefore, under the condition of P2>P1, a convex portion can be discriminated. To be concrete, when S/N ratio of signals is taken into consideration, the condition is the following.

P2−P1)>"a fixed value which can be processed electrically"

Further, it is also a preferable embodiment that P1W having great diffusivity like a white portion is made to be smaller than regular reflected light P2B reflected regularly on a position where regular reflectance is small like a black portion, and a necessary condition in this case is (P2W−P1W)>"fixed value". Under this relationship, it is possible to discriminate a convex portion on a card, independently of a color and reflectance of the card.

Expression (1) is substituted to obtain the following expression.

$$\frac{S}{\pi R^2} \gamma_1 P_0 - P_{1w} > \text{Fixed value}$$

By adjusting R representing a distance from card 507 to condenser lens 503 and adjusting S representing an effective area of the lens so that the expression above may hold, it is possible to discriminate a convex portion easily.

Further, in the present embodiment, many spots on card 107 can be measured simultaneously because of an arrangement wherein a linear light is irradiated by light-irradiating means 501 on card 107 to be received by array-shaped PD 505.

Incidentally, in the Embodiments 1–13 stated above, there has been explained an example wherein a convex portion or a concave portion on a card is formed through embossing method. However, it is also naturally possible to form a concave portion or a convex portion on a card through a method other than the embossing method.

A character (line) formed by a convex portion or a concave portion in the invention is one indicating the state of one side of a card under observation, and it is natural that the invention also includes one wherein a character (line) is formed by unevenness, like an occasion wherein an embossed character (line) is provided when both sides of a card are observed.

Incidentally, in the explanation of the aforesaid embodiment, "direction crossing" is preferably the direction which crosses almost vertically.

Effect of the Invention

As stated above, in the invention according to Structure 3-1, when a character is formed by a concave portion, if a tip portion of a light-shielding means is provided to be in the vicinity of the surface (flat portion) of a card, regular reflected light and diffused light from the flat portion are cut by the light-shielding means more, compared with regular reflected light and diffused light from the concave portion, and thereby, effective incident light is subjected to changes of its central position and angle to arrive at a light-receiving means.

Therefore, it is easy to discriminate between a flat portion and a concave portion even in the case of a card having poor reflectance for light.

Further, when a character is formed by a convex portion, if a tip portion of a light-shielding means is provided to be in the vicinity of the convex portion of a card, regular reflected light and diffused light from the convex portion are cut by the light-shielding means more, compared with regular reflected light and diffused light from the flat portion, and thereby, effective incident light is subjected to changes of its central position and angle to arrive at a light-receiving means.

Therefore, it is easy to discriminate between a flat portion and a concave portion even in the case of a card having poor reflectance for light.

In the invention of Structure 3-2, it is possible to attain cost reduction by using a cylindrical lens.

In the invention of Structure 3-3, even when a light source has great intensity distribution, intensity of each spot light can be adjusted individually by an area of a lens, and thereby, it is possible to irradiate uniform spot light.

By using a micro-lens array, it is possible to use a beam size method for judging by a diameter of a beam arriving at a light-receiving means, when discriminating between a flat portion and a convex portion of a card or between a flat portion and a concave portion.

In the invention described in Structure 3-4, the light-irradiating means and the light-shielding means are arranged so that regular reflected light reflected on a flat portion may be cut by the light-shielding means and regular reflected light reflected on the concave portion may advance to the light-receiving means. Therefore, it is easy to discriminate between a flat portion and a concave portion, because it is possible to judge to be a concave portion if the regular reflected light comes, and to judge to be a flat portion if the regular reflected light does not come.

In the invention described in Structure 3-5, the light-irradiating means and the light-shielding means are arranged so that diffused light reflected on a flat portion may be cut by the light-shielding means and only diffused light from the concave portion may advance to the light-receiving means. Therefore, it is easy to discriminate between a flat portion and a concave portion, because it is possible to judge to be a concave portion if the diffused light comes, and to judge to be a flat portion if the diffused light does not come.

The diffused light is diverged uniformly in terms of a solid angle, which is different from the regular reflected light.

Therefore, the degree of freedom for the position of a light-receiving means is high, and discrimination between a flat portion and a concave portion or between a flat portion and a convex portion is possible even when a card has a warp.

In the invention described in Structure 3-6, it is possible to generate the state wherein the linear light is projected on a convex portion or a concave portion and it is not projected on a flat portion, by making the width of a linear light emitted from a light-irradiating means to be smaller than a width (preferably, the smallest width) of a convex portion or a concave portion.

It is therefore possible to discriminate between a convex portion and a flat portion or between a concave portion and a flat portion easily, and reading accuracy for a concave portion or for a convex portion is improved.

In the invention described in Structure 3-7, when a light-receiving means employs either PD which is divided in quantity of n (n is integers of 2 or more) in the linear direction of the linear light and is divided in quantity of m (m is integers of 1 or more) in the direction crossing the linear direction or PSD array wherein n pieces are arranged in the linear direction of the linear light, it is possible to obtain central position information not only for intensity of light to be received but also for brightness of light to be received, and reading accuracy for a flat portion and a concave portion or a flat portion and a convex portion is improved.

In the invention described in Structure 3-8, a light-shielding means is provided to be movable in the direction which almost crosses the surface of the card so that it may be brought into contact with the surface of the card, thereby, even when the card is warped or even when a thin IC chip is provided on the surface of the card, the light-shielding means can move by following the surface of the card to conduct light-shielding, and reading accuracy for a flat portion and a concave portion or for a flat portion and a convex portion is improved.

In the invention described in Structure 3-9, there is provided a contact member which is brought into contact with portions other than the card so that a clearance may be formed between an end surface facing the card and the surface of the card, thereby, even when the card is warped or even when a thin IC chip is provided on the surface of the card, the light-shielding means does not interfere with the card and reading for a flat portion and a concave portion or for a flat portion and a convex portion can be conducted.

In the invention described in Structure 3-10, if an arrangement is made so that light from a flat portion of a card irradiates a light-receiving surface on one side of halved light-receiving surfaces, while light from a convex portion or a concave portion irradiates both light-receiving surfaces of halved light-receiving surfaces, or conversely, light from a flat portion of a card irradiates both light-receiving surfaces of halved light-receiving surfaces, while light from a convex portion or a concave portion irradiates a light-receiving surface on one side of halved light-receiving surfaces, it is possible to obtain signals which have no connection with intensity of light, by taking a value of (A−B)/(A+B) when A and B represent respectively output of halved light-receiving surfaces, thus, a convex portion or a concave portion can be read accurately even when reflectance for light on the surface of the card is lowered.

When a circuit for conducting division of (A−B)/(A+B) is complicated and expensive, APC (automatic power control) is applied on a light source so that output of A or B may be constant, and a value of (A−B) only is outputted. This makes it possible to obtain the results which are the same as the division on a false basis.

Further, if a light-receiving surface is divided in an asymmetrical way, sensitivity is further enhanced.

In the invention described in Structure 3-11, when two portions (for example, a black portion and a white portion) each having different reflectance are formed on the card by means of printing or the like, there is a fear that even a flat portion is misjudged to be a convex portion or a concave portion. However, when a value of ((A+C)−B)/(A+B+C) is taken under the assumption that A, B and C represent respectively output of light-receiving surface divided into three portions, even when reflectance is changed greatly in the vicinity of a convex portion or a concave portion, output corresponding to the degree of unevenness is made without being affected by the big change of reflectance, resulting in less misjudgment.

In place of conducting division of ((A+C)−B)/(A+B+C), APC (automatic power control) is applied on a light source so that output of (A+C) or of B may be constant, and a value of (A+C)−B only is outputted. This makes it possible to obtain the results which are the same as the division on a false basis. In particular, making (A+C) to be constant makes it hard to be affected by a change of reflectance caused by various patterns on the card. On this point, the effect of the present invention is much higher than that of the invention described in Structure 3-10.

Further, a value of ((A+C)−B) only is outputted for big change of unevenness, and owing to this alone, output is greatly changed by a change of unevenness, which makes comparison between a flat surface and unevenness to be easy.

In the invention described in Structure 3-12, if two light fluxes are made to coincide with each other on either a flat portion of the card or a concave portion or a convex portion on one side, two light fluxes exist on the remote portion on the other side.

Therefore, by using a light-receiving element whose light-receiving surface is split into two or three, it is possible to detect a convex portion or a concave portion.

When light is condensed on a flat portion, if PD whose light-receiving surface is split into three is used, light is condensed on the central light-receiving surface among three split light-receiving surfaces and misjudgment to cause no misjudgment, even when two portions (for example, a black portion and a white portion) each having different reflectance are formed on the card through printing.

In the invention described in Structure 3-13, if light converging is conducted on either a flat portion of the card or a concave portion or a convex portion on one side, two light fluxes exist on the portion on the other side.

Therefore, by using a light-receiving element whose light-receiving surface is split into two or three, it is possible to detect a convex portion or a concave portion.

When light is condensed on a flat portion, if PD whose light-receiving surface is split into three is used, light is condensed on the central light-receiving surface among three split light-receiving surfaces and misjudgment to cause no misjudgment, even when two portions (for example, a black portion and a white portion) each having different reflectance are formed on the card through printing.

When realizing a telecentric optical system by using one light source, its design is somewhat difficult. However, by providing each light source, it is possible to realize an inexpensive and accurate optical system which conducts telecentric behaviors.

In the invention described in Structure 3-14, when a light flux coming out of each lens of the micro-lens array is detected through a beam size method by using PD whose light-receiving surface is split into two or more concentric circles, discrimination between a flat portion and a concave portion is easy even when a change in light to be received is great and reflectance of light on the card is poor.

In the invention described in Structure 3-15, by detecting directly a flat portion and a convex portion or a concave portion of the card, discrimination between a flat portion and a concave portion is easy even in the case of a card having poor reflectance of light.

In the invention described in Structure 3-18, by detecting directly a flat portion and a convex portion or a concave portion of the card, discrimination between a flat portion and a concave portion or a convex portion is easy despite the card having poor reflectance of light.

Due to the contact means which is provided to be in contact with a card having on its surface a character formed by a convex portion or a concave portion, and in which plural contact type displacement detection sensors are arranged on a two-dimensional basis on at least a portion where the character is formed, detection can be conducted at a time, and a conveyance means which conveys at least one of the card and the contact means is made to be unnecessary.

In the invention described in Structure 3-19, among light irradiated on the card, light reflected on the flat portion other than a convex portion or a concave portion is condensed by the converging lens and advances to the light-receiving means, while, light reflected on a convex portion or a concave portion advances to a destination other than the light-receiving means, especially in the case of a curved surface which is different from a flat surface of a flat portion, such as the case where the sectional form on the surface is almost a circular arc like a convex portion or a concave portion formed through embossing.

Accordingly, the portion where the light-receiving means does not receive light, or the portion where the light-receiving signals are small can be judged in terms of existence as a convex portion or a concave portion on the card.

In the invention described in Structure 3-20, by using linear light and by receiving reflected light with array-shaped PD, it is possible to measure multiple locations on a straight line on the card simultaneously.

In the invention described in Structure 3-21, when light is irradiated on a card, reflected light is composed of regular reflected light which is reflected in the direction at an angle for the normal line on the surface of the card, said angle being identical to that for incident light irradiated, and of diffused light.

Since the diffused light from a flat portion and that from a convex portion or a concave portion are in the same intensity in any direction ideally (actually, they are not exactly the same because of a certain extent of directivity), the diffused light from a convex portion or a concave portion enters a light-receiving means through a converging lens. On the other hand, regular reflected light from a convex portion or a concave portion does not pass through the converging lens and does not enter the light-receiving means.

In the invention, intensity of regular reflected light from a flat portion is made to be greater than that of diffused light from a convex portion or a concave portion, which make it possible to discriminate between a flat portion and a convex portion or a flat portion and a concave portion. Incidentally, the greater is the difference of intensity, the easier is the discrimination.

Disclosed embodiment can be varied by a skilled person without departing from the spirit and scope of the invention.

What is claimed is:

1. A surface displacement detecting apparatus for detecting a surface displacement due to a concavity, a convexity or a hole in a surface of a detection object, comprising:
   a light shielding plate having an end portion;
   a light irradiating device provided at one side of the light shielding plate and to emit a light beam toward the surface of the detection object;
   a conveyor configured to convey at least one of the detection object and the light irradiating device relative to the other one in a conveying direction so that the surface of the detection object passes proximal to the end portion of the light shielding plate to define a gap between the surface of the detection object and the end portion of the light shielding plate, the light shielding plate being located in a direction perpendicular to the conveying direction; and
   a light receiving device provided at an opposite side of the light shielding device, the light receiving device having a light receiving surface to receive the light beam having passed through the gap and sense an intensity of the light beam,
      wherein the light beam reflected from the surface of the detection object is blocked by the light shielding plate or allowed to pass through the gap between the surface of the detection object and the end portion of the light shielding plate depending on the surface displacement of the detection object, and
      wherein the light receiving device is configured to receive the light beam at a different portion of the light receiving surface depending on the surface displacement of the detection object so that the surface displacement is detected based on the portion of the light receiving surface and the intensity of the light beam.

2. The surface displacement detecting apparatus of claim 1, wherein the light irradiating device comprises a light source and an optical element to irradiate the detection object with the light emitted from the light source and the light receiving device comprises a condenser lens to condense at least one of regular reflection light and diffuse reflection light from the surface of the detection object and a light receiving element to receive the condensed light.

3. The surface displacement detecting apparatus of claim 2, wherein the light irradiating device shapes the light in a line and irradiates the detection object with the line-shaped light.

4. The surface displacement detecting apparatus of claim 3, wherein the light receiving elements are a PSD array in which n pieces of PSD are arranged in a direction along the line-shaped light or PD which is split into n pieces in a direction along the line-shaped light and m pieces in a direction perpendicular to along the line-shaped light, where n is an integer not less than 2 and into m is an integer not less than 1.

5. The surface displacement detecting apparatus of claim 2, wherein the optical element is a cylindrical lens.

6. The surface displacement detecting apparatus of claim 2, wherein the light irradiating device forms a plurality of spot light aligned in a straight line as the light and irradiates the detection object with the plurality of spot light.

7. The surface displacement detecting apparatus of claim 6, wherein the optical element is a micro lens array.

8. The surface displacement detecting apparatus of claim 6, wherein the light receiving elements are a PSD array in which n pieces of PSD are arranged in a direction along the plurality of aligned spot light or PD which is split into n pieces in a direction along the plurality of aligned spot light and into m pieces in a direction perpendicular to along the plurality of aligned spot light, where n is an integer not less than 2 and m is an integer not less than 1.

9. The surface displacement detecting apparatus of claim 2, wherein the surface displacement detecting apparatus detects the concavity, the convexity or the hole from a light receiving position on the light receiving device.

10. The surface displacement detecting apparatus of claim 9, wherein the light receiving position on the light receiving element displaces in a direction parallel to the light receiving element.

11. The surface displacement detecting apparatus of claim 2, wherein the light receiving device comprises a plurality of light receiving elements aligned in a straight line as the light receiving element or the light receiving element is split into a plurality of light receiving elements aligned in a straight line.

12. The surface displacement detecting apparatus of claim 2, wherein the light receiving elements are a PSD array in which n pieces of PSD are arranged in a predetermined direction or PD which is split into n pieces in a predetermined direction and into m pieces in a direction perpendicular to the predetermined direction, where n is an integer not less than 2 and m is an integer not less than 1.

13. The surface displacement detecting apparatus of claim 1, wherein the detection object comprises a flat surface and the concavity and the light irradiating device, the light shielding device and the light receiving device are arranged such that light reflected from the flat surface is shielded by the light shielding device and light reflected from the concave proceeds to the light receiving device.

14. The surface displacement detecting apparatus of claim 1, wherein the detection object comprises a flat surface and the concavity and the light irradiating device, the light shielding device and the light receiving device are arranged such that light diffused from the flat surface is shielded by the light shielding device and light diffused from the concave proceeds to the light receiving device.

15. The surface displacement detecting apparatus of claim 1, wherein a width of the light on the detection object is smaller than a width of the concavity, the convexity or the hole.

16. The surface displacement detecting apparatus of claim 1, wherein the light shielding device is shiftable in a direction crossing the surface of the detection object and the light shielding device is brought in contact with the detection object.

17. The surface displacement detecting apparatus of claim 1, wherein the light shielding device has an edge surface facing the detection object and is arranged to form a space between the edge surface and the detection object.

18. The surface displacement detecting apparatus of claim 1, wherein the detection object is a card having the concavity, the convexity or the hole.

19. The surface displacement detecting apparatus of claim 1, wherein a range of the displacement of the concavity, the convexity or the hole on the detection object is not larger than 1.0 mm.

20. The surface displacement detecting apparatus of claim 1, wherein the surface displacement detecting apparatus detects an amount of the surface displacement of the concavity, the convexity or the hole.

21. The surface displacement detecting apparatus of claim 1, wherein the light receiving device receives at least one of regular reflection light and diffuse reflection light from the surface of the detection object.

* * * * *